(12) United States Patent
Benton

(10) Patent No.: US 7,727,240 B1
(45) Date of Patent: Jun. 1, 2010

(54) METHOD AND SYSTEM FOR SECURING AN INTRAMEDULLARY NAIL

(76) Inventor: Blake Benton, 29 Schuyler Ave., Cragsmoor, NY (US) 12420

( * ) Notice: Subject to any disclaimer, the term of this patent is extended or adjusted under 35 U.S.C. 154(b) by 390 days.

(21) Appl. No.: 11/355,030

(22) Filed: Feb. 15, 2006

(51) Int. Cl.
A61B 17/58 (2006.01)
A61B 17/60 (2006.01)
A61F 2/00 (2006.01)

(52) U.S. Cl. .............................. 606/98; 606/62; 606/99

(58) Field of Classification Search .......... 606/62–64, 606/96–98, 104, 916, 67, 86 R, 99, 102
See application file for complete search history.

(56) References Cited

U.S. PATENT DOCUMENTS

| | | | |
|---|---|---|---|
| 4,667,664 A * | 5/1987 | Taylor et al. ................... | 606/64 |
| 4,911,153 A * | 3/1990 | Border ......................... | 606/98 |
| 4,969,889 A | 11/1990 | Greig | |
| 5,403,322 A | 4/1995 | Herzenberg et al. | |
| 5,411,503 A | 5/1995 | Hollstien et al. | |
| 5,433,720 A * | 7/1995 | Faccioli et al. ................. | 606/87 |
| 5,514,145 A | 5/1996 | Durham et al. | |
| 5,584,838 A | 12/1996 | Rona et al. | |
| 5,620,449 A * | 4/1997 | Faccioli et al. ................. | 606/98 |
| 5,951,561 A | 9/1999 | Pepper et al. | |
| 6,183,477 B1 | 2/2001 | Pepper | |
| 6,216,028 B1 | 4/2001 | Haynor et al. | |
| 6,616,670 B2 | 9/2003 | Simon et al. | |
| 6,783,535 B2 * | 8/2004 | Deloge et al. ................. | 606/98 |
| 6,932,819 B2 | 8/2005 | Wahl et al. | |
| 7,056,322 B2 * | 6/2006 | Davison et al. ................ | 606/98 |
| 2003/0135211 A1* | 7/2003 | Cho ............................ | 606/62 |
| 2003/0220651 A1 | 11/2003 | Pusnik et al. | |
| 2004/0010252 A1 | 1/2004 | Zander et al. | |
| 2004/0011365 A1 | 1/2004 | Govari et al. | |
| 2004/0034355 A1 | 2/2004 | Govari et al. | |
| 2004/0039393 A1 | 2/2004 | Robioneck et al. | |
| 2004/0059329 A1 | 3/2004 | Zander | |
| 2004/0088136 A1 | 5/2004 | Ashe | |
| 2004/0138671 A1 | 7/2004 | Zander et al. | |
| 2005/0020908 A1 | 1/2005 | Birkenbach et al. | |
| 2005/0049820 A1 | 3/2005 | Kirsch et al. | |
| 2005/0075561 A1 | 4/2005 | Golden | |
| 2005/0075562 A1 | 4/2005 | Szakelyhidi | |

(Continued)

FOREIGN PATENT DOCUMENTS

FR 2647006 A1 * 11/1990

(Continued)

*Primary Examiner*—Eduardo C Robert
*Assistant Examiner*—Ellen C. Hammond
(74) *Attorney, Agent, or Firm*—Hoffmann & Baron, LLP

(57) ABSTRACT

A device, method and system adapted to determine a targeting position on a surgically implantable nail adapted to be used in internal fixation of a bone, the nail comprising a distal end and a proximal end, the device including an extension rod comprising a longitudinal axis and adapted to be detachably coupled to the proximal end of the nail, a bridge member adjustably secured to the extension rod and extending radially from the longitudinal axis of the extension rod, a position of the bridge member on the extension rod being rotationally and longitudinally adjustable with respect to the longitudinal axis of the extension rod, and a targeting arm adjustably coupled to the bridge member and extending from the bridge member toward the distal end of the locking nail, the targeting arm comprising a drill guide.

29 Claims, 24 Drawing Sheets

U.S. PATENT DOCUMENTS

| | | |
|---|---|---|
| 2005/0080335 A1 | 4/2005 | Simon et al. |
| 2005/0080427 A1 | 4/2005 | Govari et al. |
| 2005/0203520 A1 | 9/2005 | Volzow |
| 2005/0261698 A1 | 11/2005 | Powell |

FOREIGN PATENT DOCUMENTS

| | | |
|---|---|---|
| FR | 2689751 A1 * | 10/1993 |
| GB | 2258154 A * | 2/1993 |
| JP | 2004065977 A * | 3/2004 |

\* cited by examiner

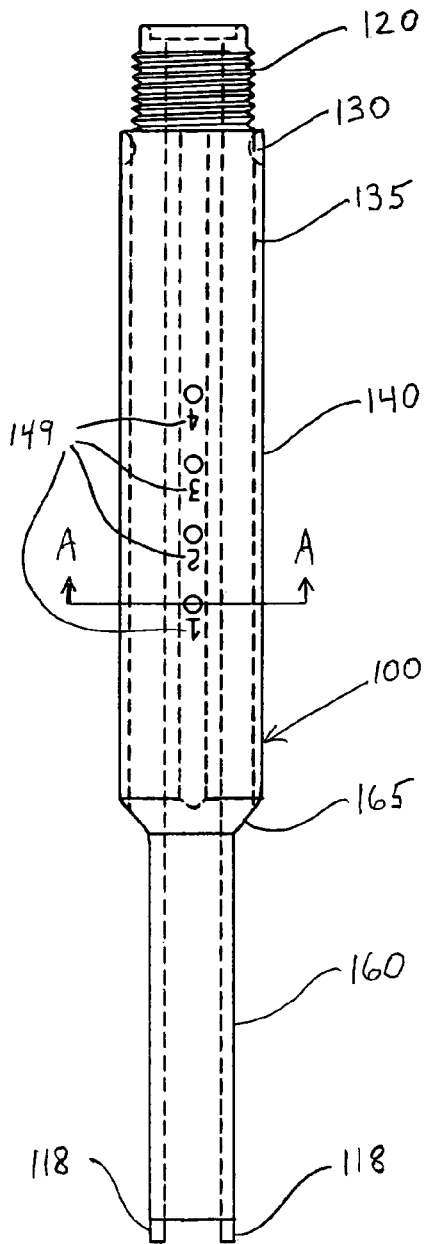
Fig. 3b
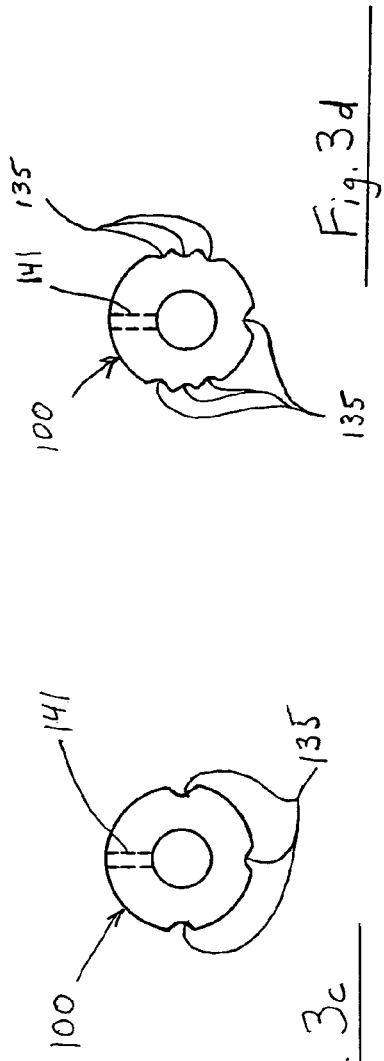
Fig. 3d
Fig. 3c
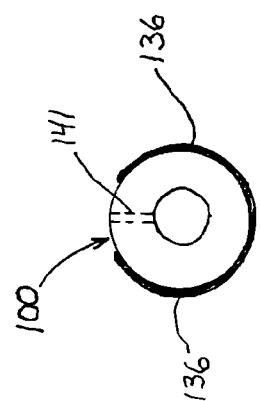
Fig. 3e

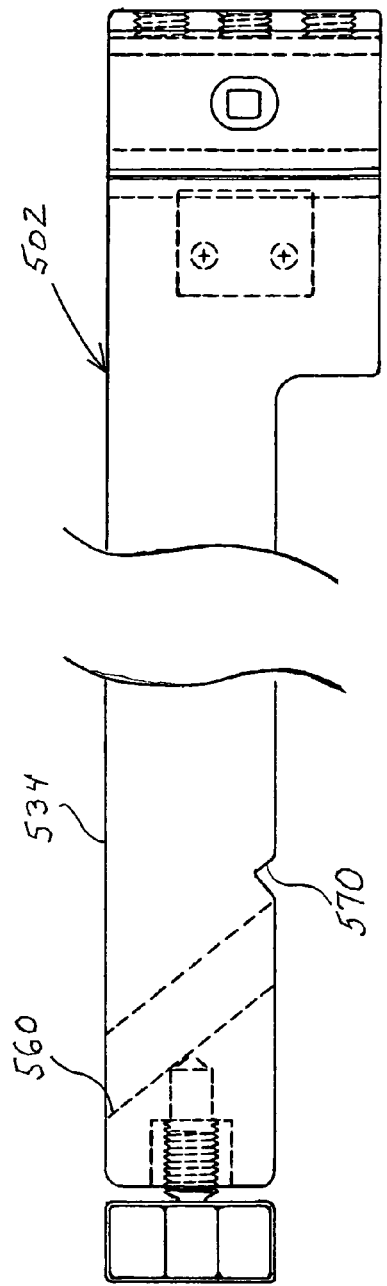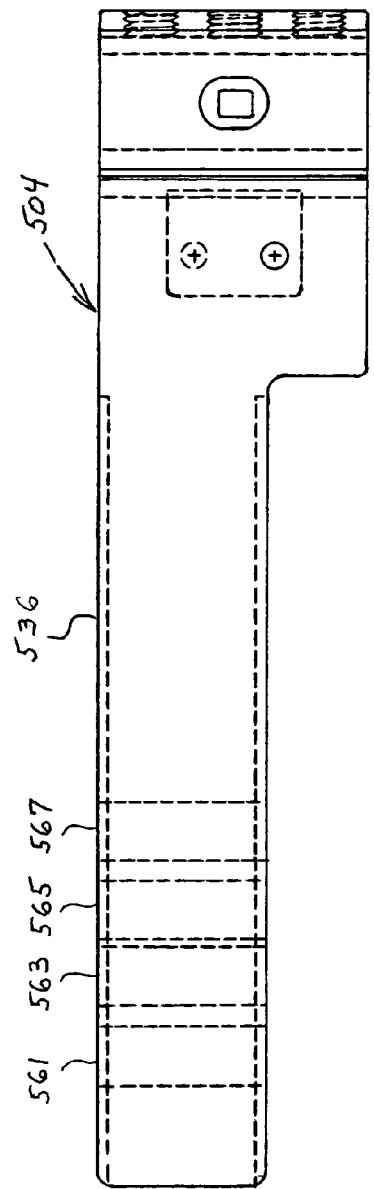

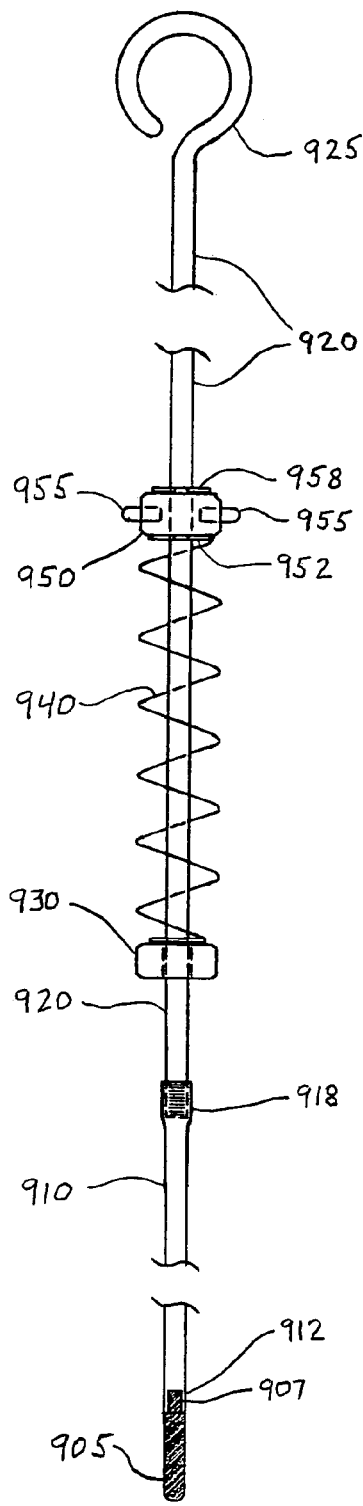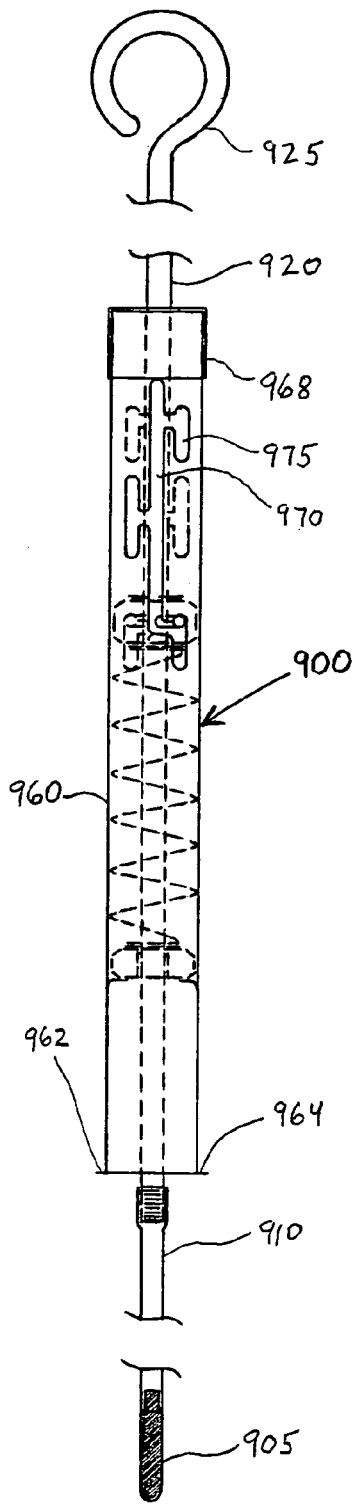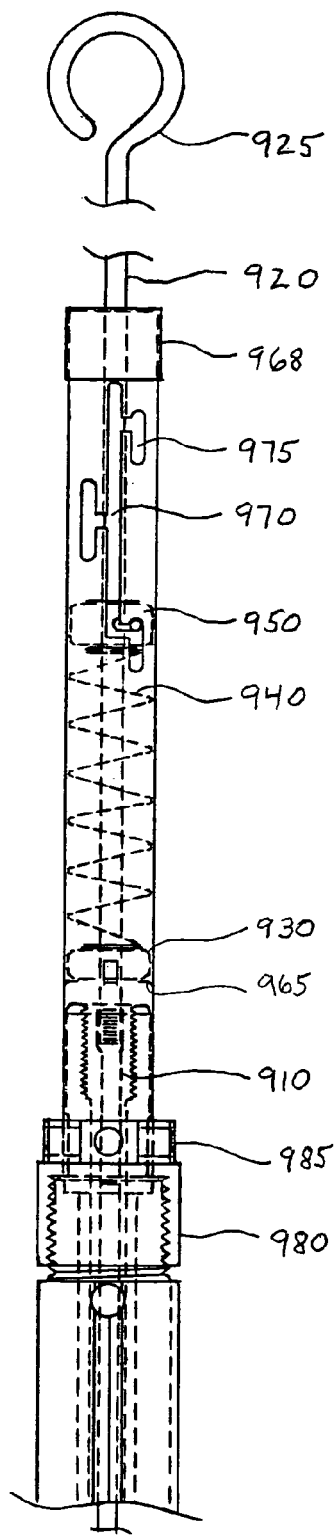

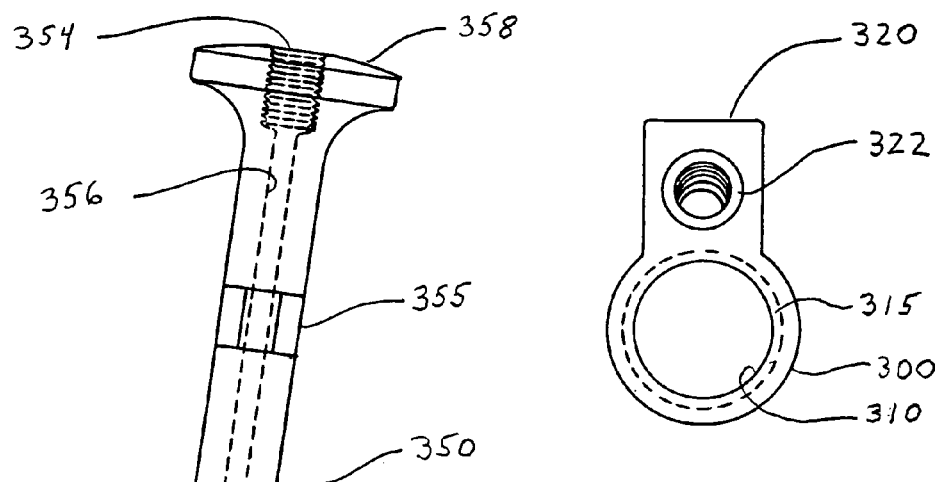
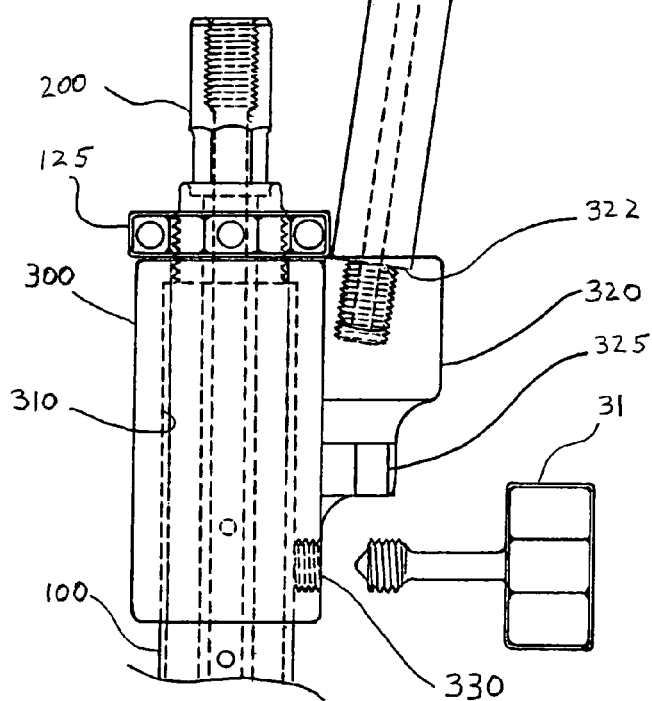
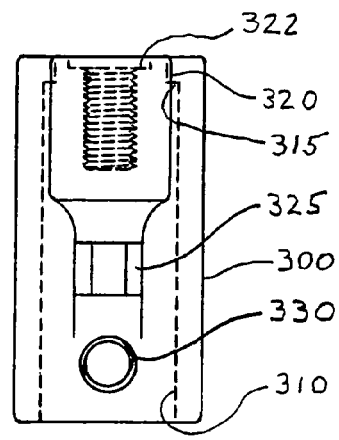
Fig. 26c
Fig. 26a
Fig. 26b

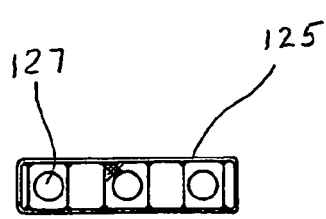
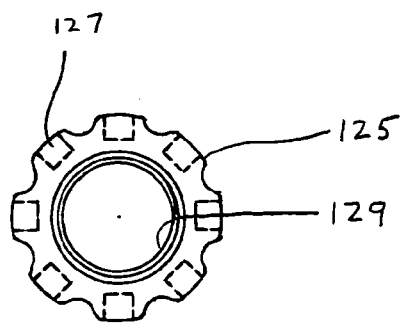
Fig. 27a
Fig. 27b
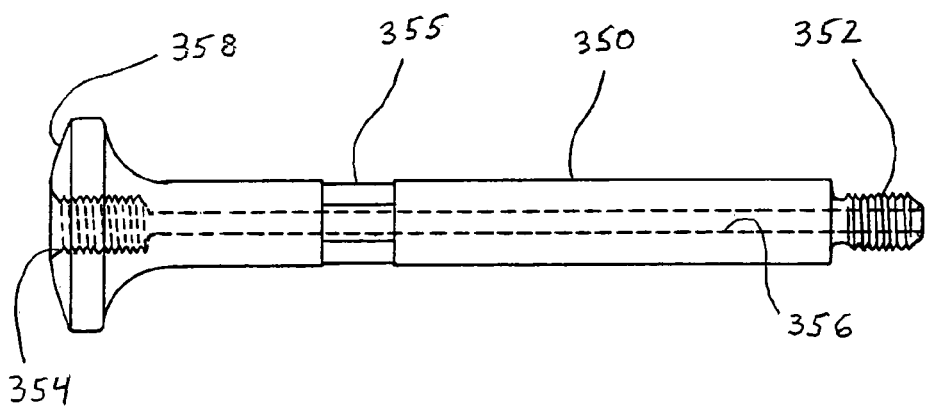
Fig. 28a
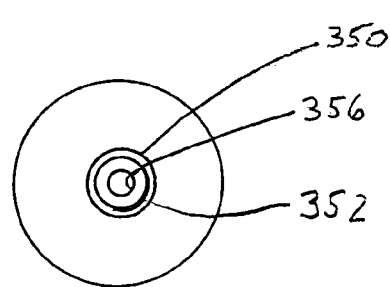
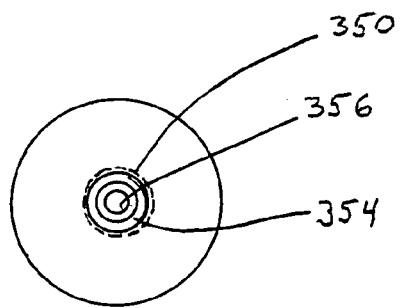
Fig. 28b
Fig. 28c

METHOD AND SYSTEM FOR SECURING AN INTRAMEDULLARY NAIL

BACKGROUND OF THE INVENTION

1. Field of the Invention

The present invention relates to the implantation of an intramedullary nail (IMN) for repair of long bone internal fractures. More specifically, the present invention relates to a system and method for targeting and placement of locking members in an IMN by means of magnetic and mechanical guidance. The present invention provides guidance for both proximal and distal targeting in an IMN.

2. Brief Description of the Related Art

In order to repair long bone fractures it is often necessary to use implants known as intramedullary nails (IMN). For example, an IMN can be used to repair an internal fracture of the femoral or tibial shafts. Advantages associated with the usage of an IMN include providing sufficient stability to maintain alignment and length, and limit rotation of the fracture site. Further advantages include minimally invasive techniques, reduced hospitalization, earlier postoperative ambulation, and earlier active range of motion (ROM) when compared to some conventional casting or external fixation methods.

The standard operating procedure for the fixation of long bone fractures with an IMN consists of the implantation of the IMN, an elongated, rod-like, metallic orthopedic appliance into the affected medullary canal of a given long bone. The clinician typically starts with an incision and thereafter creates an opening in the proximal or distal end (antegrade or retrograde) of a given long bone, thereby providing access to the affected medullary canal in which the IMN is then implanted. One goal in IMN treatment is fracture reduction so that near anatomic alignment takes place under stabilized conditions, often facilitated by means of locking members, for example, locking screws that are integrated with an IMN.

A given IMN is prefabricated, for example, with locking holes that are located in the general vicinity of the proximal and distal ends of the IMN. These locking holes can accept one or more interlocking screws. The locking screws when interlocked with an IMN are designed to stabilize the fracture and fix the bone relative to the implanted IMN.

Proximal interlocking screws are relatively easy to place in their corresponding locking holes due in part to minimal deformation at the proximal end of an implanted IMN and the use of rigid targeting guides that are fixed to the proximal end of the selected IMN. These external proximal targeting guides have integral guide bores oriented and positioned inline with the effective central axis of the proximal locking holes, thus facilitating proximal locking. In contrast, one of the most difficult procedural aspects of implanting an IMN has been the location, alignment, drilling and subsequent placement of the distal locking screws. This difficulty stems in part from distal deformations that occur in some IMN's when they are implanted in the affected medullary canal.

At least one contemporary study has demonstrated that a larger-diameter IMN, (cannular 13-mm) can, upon implantation, exhibit lateral deformations of 21.5±7.9 mm (range: 26.4 mm), dorsal deformations of 0.4±9.8 mm (range: 30.1 mm), and rotational deformations about the longitudinal axes of 10.0±3.1 degrees (range: 7.8 degrees). Such IMN distal end deformations make it difficult to use and rely on conventional targeting guides. Also, tight manufacturing tolerances that are needed between the IMN and the interlocking screws adding to the difficulty.

Attempts have been made to compensate for the above-mentioned deformations, through the use of hand-held powered magnetic targeting systems. Such techniques can include the use of a probe inserted into a cannular IMN. Once the probe in such a system is in place near the desired IMN's distal locking hole position, a hand-held guide is used to maintain proper alignment of a drill, and an electromagnetic display unit connected to the probe displays visual images that graphically indicate the manner in which the guide must be moved to bring it into proper alignment. Unfortunately, to ensure the drill hole is actually made in the desired location, such a system must still rely on the steady hand of the orthopedic surgeon, intense eye-hand coordination and is subject to the inaccuracies related to drill walk.

Unfortunately, contemporary apparatus fail to solve the problem of effectively targeting the distal locking hole positions. The combination of the deformation of the implanted IMN, the slight shake that is natural in hand-held instruments, the drift that often occurs with contemporary drills when drilling through bone, and other factors make it difficult to actually drill a hole that properly aligns with a distal locking hole position. Also, contemporary devices do not provide a reliable overall system for targeting and securing both proximal and distal locking hole positions.

SUMMARY OF THE INVENTION

The present invention solves the distal targeting needs that are so prevalent in the market today. Also, the present invention includes guided proximal targeting mechanisms of relatively simple design that can be used with most contemporary intramedullary nails (IMN's). In this way, virtually any IMN locking position can be located in order to properly secure the implanted IMN. Also, the invention provides a simple and efficient procedure for securing the IMN.

Another aspect of the present invention is to provide a system and method that compensates for nail deflection and the errors caused by micro-movement inherent in this manually driven procedure. Also, the present invention can drastically reduce x-ray exposure to the clinician, staff and patient. Further, the present invention can reduce the time required in the operating room, which helps both the patient and the medical practitioners performing the procedure. Further, the present invention is universally adaptable to most all IMN's on the market, anticipates all guided proximal and distal locking positions including those many not generally employed.

One embodiment of the current invention is directed to a device adapted to determine a targeting position on a surgically implantable nail adapted to be used in internal fixation of a bone, the nail comprising a distal end and a proximal end, the device including an extension rod comprising a longitudinal axis and adapted to be detachably coupled to the proximal end of the nail, a bridge member adjustably secured to the extension rod and extending radially from the longitudinal axis of the extension rod, a position of the bridge member on the extension rod being rotationally and longitudinally adjustable with respect to the longitudinal axis of the extension rod, and a targeting arm adjustably coupled to the bridge member and extending from the bridge member toward the distal end of the locking nail, the targeting arm comprising a drill guide.

Another aspect of the current invention provides the above device wherein the position of the targeting arm on the bridge member can be adjustable to vary the distance between the targeting arm and the extension rod. Also, the drill guide can be positioned closer to the distal end of the nail than to the proximal end of the nail. Further, at least one of the orientation and position of the drill guide can be adjustable for alignment with the targeting position. Further still, the bridge member can be adapted to be secured to the extension rod in at least one of a first orientation and a second orientation, the bridge member comprising a location for coupling to the targeting arm that is closer to the distal end of the nail in the first orientation than in the second orientation. Yet further still, the targeting arm can be adapted to position a targeting console adapted to indicate alignment between the drill guide and the targeting position on the nail. Additionally, the above device can include a targeting probe adapted to be inserted through the extension rod and at least a portion of the nail.

Yet another embodiment of the current invention provides a device adapted to secure an intramedullary nail adapted to be used in internal fixation of bones, the nail comprising a distal end, a proximal end, and a targeting position, the device comprising an extension rod adapted to be detachably coupled to the proximal end of the nail, a targeting assembly adjustably secured to the extension rod, at least a portion of the targeting assembly extending toward the distal end of the nail, the targeting assembly comprising a drill guide, at least one of an orientation and position of the drill guide on the targeting assembly being adjustable, and an alignment device adapted to be removably coupled to the targeting assembly, the alignment device adapted to indicate alignment of the drill guide with the targeting position.

Another aspect of the current invention provides the later-mentioned device wherein a position of the targeting assembly relative to the extension rod can be rotationally and longitudinally adjustable with respect to a longitudinal axis of the extension rod. Also, a position of the targeting assembly relative to the extension rod can be rotationally and longitudinally adjustable with respect to a longitudinal axis of the extension rod. Further, the targeting assembly can comprise a bridge portion and an extension portion, the bridge portion being adapted to be adjustably secured to the extension rod, the extension portion being adapted to be adjustably secured to the bridge portion and extending from the bridge portion toward the distal end of the nail. Further still, a distal end of the extension portion can be closer to the distal end of the nail than to the proximal end of the nail. Yet further still, the bridge portion can be adapted to be secured to the extension rod in at least one of a first orientation and a second orientation, the bridge portion comprising a location for coupling to the extension portion that is closer to the distal end of the nail in the first orientation than in the second orientation. Additionally, the later-mentioned device can include a targeting probe adapted to be inserted through the extension rod and at least a portion of the nail.

Yet another embodiment of the current invention provides a method of targeting a fastener position on a surgically implantable nail adapted to be used in internal fixation of bones comprising attaching an extension rod to a proximal end of the nail, securing a targeting assembly to the extension rod, a portion of the targeting assembly extending toward a distal end of the nail, the targeting assembly comprising a drill guide and a rotational feature adapted to change at least one of orientation and position of the drill guide with respect to the targeting assembly, coupling an alignment pin to the drill guide, adjusting the rotational feature to a pre-surgical position such that the drill guide is aligned with the fastener position, indicating the pre-surgical position on at least one of the extension rod and the targeting assembly prior to implanting the nail surgically, disassembling at least a portion of the targeting assembly from the extension rod, and implanting the nail surgically.

Another aspect of the current invention provides the above method also comprising decoupling the alignment pin from the targeting assembly, and resecuring the targeting assembly to the extension rod such that the rotational feature is in the pre-surgical position. Additionally, the above method can include mounting an alignment device to the targeting assembly, the alignment device adapted to indicate whether the drill guide is aligned with the fastener position. Also, the rotational feature can be adjusted based on the alignment device.

These and other objectives, features, and advantages of this invention will become apparent from the following detailed description of illustrative embodiments thereof, which is to be read in connection with the accompanying drawings.

BRIEF DESCRIPTION OF THE DRAWINGS

FIGS. 3a-f show plan, left side, cross-sectional, two alternate embodiment cross-sectional, and top views, respectively, of a nail adapter in accordance with an embodiment of the current invention.

FIGS. 8a-b show plan and top views, respectively, of an alternate embodiment of a targeting arm in accordance with an embodiment of the current invention.

FIGS. 9a-b show plan and top views, respectively, of a further alternate embodiment of a targeting arm in accordance with an embodiment of the current invention.

FIGS. 13a-c show plan, top and bottom views, respectively, of a target sensor probe sub-assembly in accordance with an embodiment of the current invention.

FIGS. 14a-c show plan, top and bottom views, respectively, of a target sensor probe sub-assembly seen in FIGS. 13a-c, but with additional elements included thereon in accordance with an embodiment of the current invention.

FIGS. 15a-b show plan and top views, respectively, of a complete target sensor probe sub-assembly in accordance with an embodiment of the current invention.

FIGS. 26a-c show plan, bottom and right side views, respectively, of a tamping collar assembly in accordance with an embodiment of the current invention.

FIGS. 27a-b show plan and top views of a locking nut in accordance with an embodiment of the current invention.

FIGS. 28a-c show plan, right side and left side views, respectively, of a tamping rod in accordance with an embodiment of the current invention.

DETAILED DESCRIPTION OF THE PREFERRED EMBODIMENTS

The drawings show a device embodying the principles and concepts of the present invention. It should be noted that although the figures are directed to the preferred embodiment, other applications of the instant invention are anticipated, as discussed more fully below.

Figure 1:
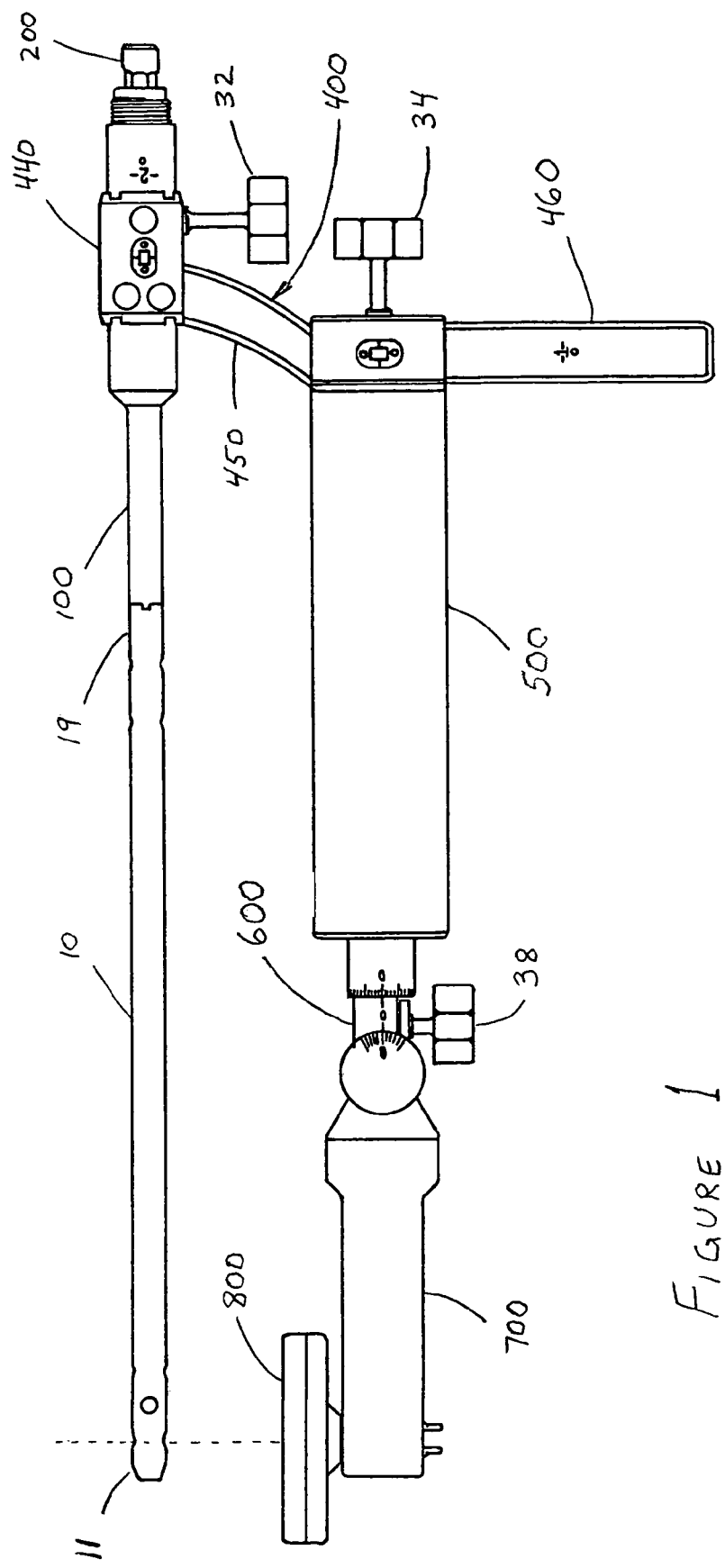
FIG. 1 shows a plan view of an assembly of a portion of an intramedullary nail targeting and securing system in accordance with an embodiment of the current invention.

FIG. 1 shows major portions of a modular assembly for an intramedullary nail (IMN) securing system. An IMN 10 is shown having a distal end 11 depicted on the left side and an opposing proximal end 19. In one assembled embodiment, a nail adapter 100 is preferably coupled to the proximal end 19 of the IMN 10 by a coupler rod 200 that fits inside and extends the length of the nail adapter 100. In the assembled state, the coupler rod 200 is preferably threaded and engaged at one end with the IMN 10, while holding the coupler rod 200 in place with flange elements 210 at an opposite end. A bridge adapter 400 preferably has a cylindrical mounting collar 440 at one end that fits onto the nail adapter 100. A central portion 450 of the bridge adapter 400 preferably extends away from the central longitudinal axis of the IMN 10 at an angle, which is further discussed below. Also, the bridge adapter 400 preferably has a mounting shaft 460 at a second end. A distal targeting arm 500 is preferably coupled at one end to the mounting shaft 460 of the bridge adapter 400. The distal targeting arm 500 is preferably intended for distal targeting applications. Preferably mounted on the other end of the distal targeting arm 500, is a head coupling 600. The head coupling 600 also preferably provides a pivotal mount for the targeting head 700. It is the targeting head 700 that preferably holds the targeting console 800. In this assembled state, a targeting probe can be inserted through the nail adapter 100 and coupler rod 200 and into the cannular portion of the distal end of the IMN 10.

Various fixing screws in the present system can be potentially made to be interchangeable such as in the case of those seen in FIG. 1. However, in an alternative embodiment, a different fixing screw profile may be beneficial. Fixing screw 38 has a flange at its base that is preferably present for the use in one application of the present system. However, a non-flange design, as in screws 32, 34, could be used. Alternatively, all screws could have a similar flange design. It is further understood in the art that further alternative set-screws could be exploited throughout the present system as well.

The magnetic targeting aspects of the present system along with the mechanical elements related to the distal targeting, are not typically used for targeting proximal targeting positions. Proximal targeting holes are preferably targeted with proximal targeting arms that are preferably mounted in place of the distal targeting arm 500 and its more distal connected members 600, 700, 800. Nail deformation is not usually a limiting factor in proximal locking.

The modular apparatus shown in FIG. 1 (referred to herein as the targeting arm assembly) is preferably assembled starting with a selected IMN 10. The IMN 10 is then coupled to a coupler rod 200 surrounded by a nail adapter 100. Thereafter, a bridge adapter 400 is preferably mounted onto the proximal end of the nail adapter 100. Then, preferably in order, the targeting arm 500, the head coupling 600, and the targeting head 700 are added to the assembly. These portions of the targeting system are preferably assembled prior to implanting the IMN 10 in order to get an estimate of the final configuration and position of parts before initiating the operative procedure. The targeting console 800 is mounted after the IMN 10 is implanted in a patient. Special position tracking tools can be applied or markings made on the assembly, so that it can be quickly reassembled in the marked positions during the operative procedure. This can greatly reduce the time required to perform distal targeting on an IMN 10.

Once the estimated configuration of the targeting arm assembly is complete, the targeting arm distal sub-assembly is preferably removed. The distal sub-assembly consists of the bridge adapter 400, targeting arm 500, head coupling 600, and targeting head 700. Once assembled to the IMN 10, the nail adapter 100 and coupler rod 200 preferably remain attached and are used to facilitate IMN 10 implantation. In order to properly seat the IMN 10 into the medullary canal, a tamping collar 300 (see FIGS. 26a-c) can be mounted onto the cylindrical mounting portion 140 of the nail adapter 100. The tamping collar 300 installed with a tamping rod 350 in conjunction with a strike instrument such as a hammer (not shown) is one method that can be used to facilitate IMN implantation. Alternatively, bridge adapter 400 can be assembled and secured to the cylindrical mounting portion 140 of the nail adapter 100 where hand leveraging of the IMN 10 is possible.

Figure 13B:
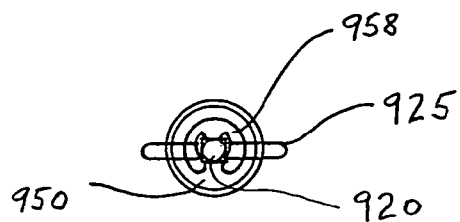
Figure 13C:
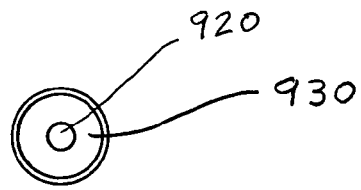
Figure 14C:
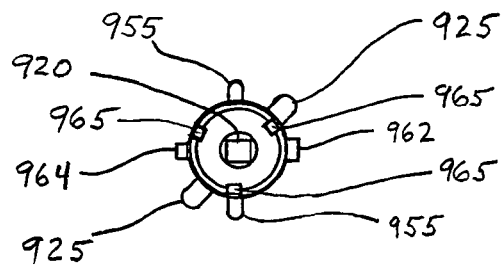
Figure 14B:
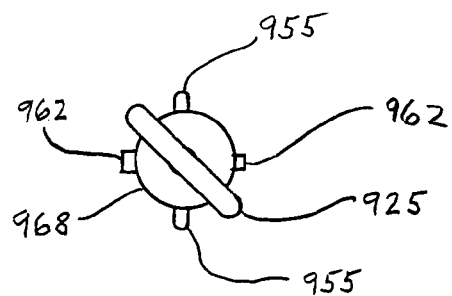
Figure 20:
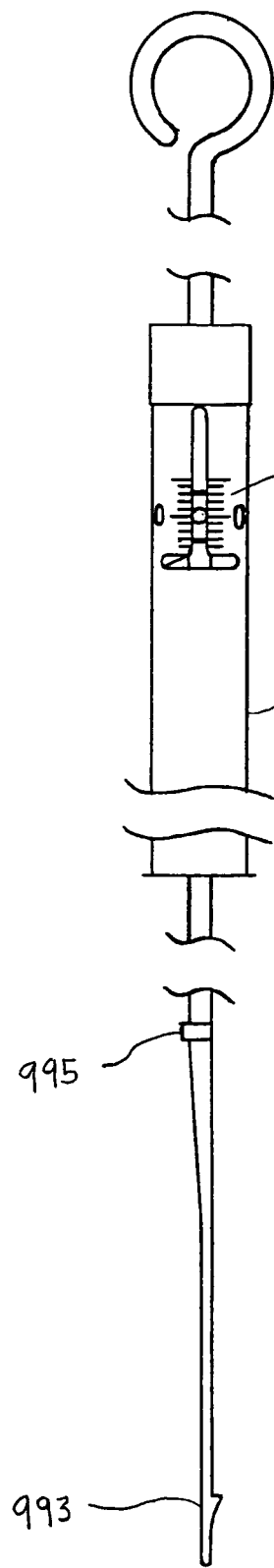
FIG. 20 shows a plan view of a sensor calibration probe in accordance with an embodiment of the current invention.
Figure 21:
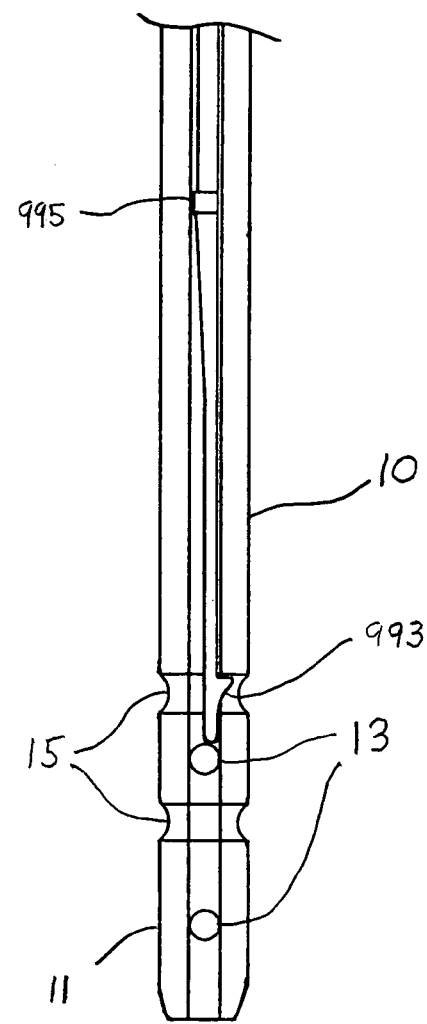
FIG. 21 shows the distal portion of a sensor calibration probe inserted in a cannular intramedullary nail in accordance with an embodiment of the current invention.

As it is understood that the IMN 10 often deforms during implantation, the distal target securing holes and/or slots in the IMN 10 can be calibrated, using the sensor calibration probe 990 (see FIGS. 20 and 21). In this way, the amount of deflection of the implanted nail can be ascertained via the sensor calibration probe 990. It is understood however that distal targeting can be performed with the other parts of this invention without the use of the sensor calibration probe 990. If desired, once the deformation causing the difference in position and orientation of the distally located locking holes and/or slots in a given IMN 10 is calibrated/gauged, then corresponding adjustments can be made to the sensor delivery probe 900. This will provide for more accurate targeting when later delivering and locating the probe. Thereafter, the targeting arm sub-assembly elements 400, 500, 600, 700 are remounted to the configuration initially estimated, as described above. Then additionally the target console 800 is preferably added at this time, as seen in FIG. 1. Thereafter, the target sensor probe assembly 900 (see FIGS. 13-15) is preferably mounted where the sensor calibration probe 990 was mounted. Thus, a target sensor can then be inserted into the cannular portions of the coupler rod 200 and the IMN 10, at least to the desired distal targeting position. Thereafter, the targeting head 700 position is readjusted and fixed based on the indications of its targeting console 800 display. Once the drilling position is properly aligned, the targeting arm 500 can be rapidly removed along with the other more distal elements 600, 700, 800 secured thereto. The console 800 is preferably removed from the targeting head 700 during targeting arm removal. Thus, for example, providing space to mark the indicated incision point and perform incision/resection of skin/tissue. Once the marked incision is made, the targeting arm 500 and attached distal elements 600, 700 (not including the console 800 which was removed) are returned to their targeting positions (maintained and/or reposition by marking elements and/or a location fixing element). Then a surgical instrument, for example, a trocar or preferably a triple trocar (not shown) can be inserted in the mounting head position previously occupied by the targeting console 800. The triple trocar (not shown) once inserted should preferably extend from the targeting head 800 through the incision and preferably contact the targeted bone outer surface. A trocar can be used, among other things, as a drilling guide and provides/allows minimally invasive techniques to be applied such as tissue protection. Preferably at this point a hole is drilled through the near and far cortex of the bone that corresponds with the effective central axis of the distally targeted position. After distal locking takes place, proximal locking can commence using for example, a proximal targeting arm such as the exemplary proximal targeting arms shown in FIGS. 8 *a-b*, 9 *a-b*. The present system can exploit proximal targeting arms that could be constructed in such a way to address most existing and later conceived proximal targeting positions. Although the preferred method of the present system is to perform distal locking prior to proximal locking, a reverse or staggered locking progression can be accomplished with the present system. Pre-imbedded sensors could facilitate proximal locking before distal locking.

Figure 2:
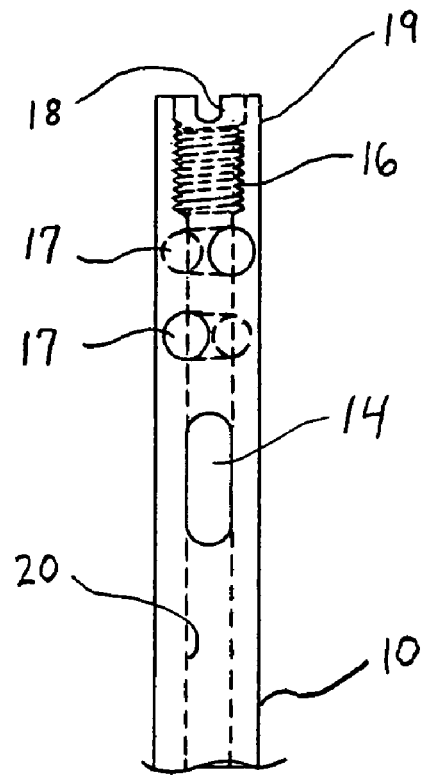
FIG. 2 shows a cannular intramedullary nail with targeting holes in accordance with an embodiment of the current invention.
Figure 2:
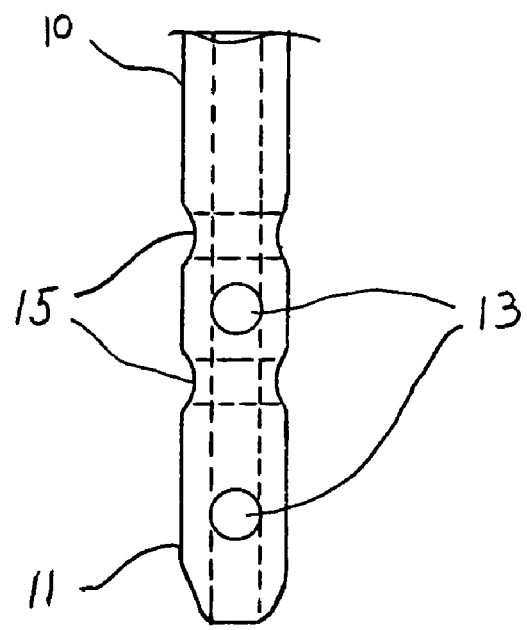

FIG. 2 shows two portions of a cannular IMN 10 that includes an inner cannular portion 20 that extends preferably its entire length. The IMN 10 shown in FIG. 2 merely demonstrates exemplary features of IMN's. However, it is understood in the art that almost any IMN could be used in connection with the present invention. A given IMN could have one or more of the features shown. Intramedullary nails can be solid, but such IMN's would preferably have pre-implanted sensors that can aid in targeting. The exact position and orientation of such sensor should be known, relative to any targeting holes or slots provided in the nail. The distal end 11 preferably includes one or more locking holes 13, although additional receiving locking holes 15 can be provided. As seen in FIG. 2, the additional locking holes 15 have a longitudinal axis, which is preferably ninety degrees different from that of locking holes 13. However, alternatively, the longitudinal axis of each of the two sets of transverse locking holes 13, 15 could be parallel or offset from one another at almost any angle. The proximal end 19 of the IMN 10 preferably includes a female threaded coupling 16 and a pair of female alignment slots 18. This female threaded coupling 16 preferably mates when assembled with the male threaded end 230 of the coupler rod 200. Also, the female alignment slots 18 preferably mate when assembled with a pair of alignment tabs 118 on the nail adapter 100. It should be understood that these and other alignment slots/tabs can be of varying profiles and color coded to facilitate proper assembly of the overall system.

The proximal end of the IMN 10 is also preferably provided with transverse locking holes 17. Many holes at the proximal end of a given IMN could be oblique as well. Additionally, shown in FIG. 2 is a longitudinal targeting slot 14. This type of slot, which traverses the entire width of the IMN 10, can also be provided at the distal end of the IMN 10. Targeting slots 14 can be used to allow some axial movement of the IMN 10 relative to the bone in which it is implanted. However, when targeting such a slot 14, a particular position within the slot is preferably targeted in order to provide the desired amount of axial movement or lack thereof.

Figure 3A:
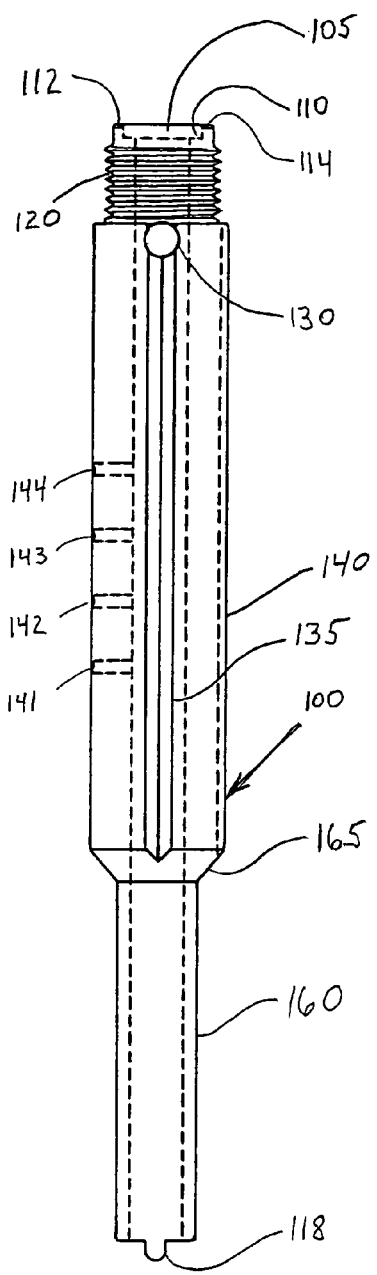

FIGS. 3*a-c* show side, top and cross sectional views, respectively, of a nail adapter 100 in accordance with a preferred embodiment of this invention. FIGS. 3*d* and 3*e* show alternative cross-sectional views from that shown in FIG. 3*c*. The nail adapter 100 is preferably coupled to a selected IMN 10 by means of a cannular coupler rod 200. The first end of the nail adapter 100 preferably has at least one fixing screw groove 135 that is formed along the greater longitudinal length of the cylindrical mounting portion 140. The fixing screw grooves 135 are intended to receive the fixing screw 32, which can secure other elements onto the cylindrical mounting portion 140. FIG. 3*c* shows an embodiment including three fixing screw grooves 135 formed onto the cylindrical mounting portion 140. Alternatively, as seen in FIG. 3*d*, many more fixing screw grooves 135 can be formed along the perimeter of the cylindrical mounting portion 140. In yet a further alternative embodiment seen in FIG. 3*e*, a portion of the cylindrical mounting portion 140 can be formed with a texture or coated with a substance or material that is adapted to increase the frictional engagement between the tip of the fixing screw 32 and the cylindrical mounting portion 140, and can be void of grooves while still having transverse proximal targeting positions indicated.

FIGS. 3*a* and 3*b* also show that the cylindrical mounting portion 140 is the widest circumferential area of the first end of the nail adapter 100. The nail adapter 100 also preferably has at its first end one or more visibly numbered, by position numbers 149, transverse targeting position bores 141, 142, 143, and 144. Further, the first end of the nail adapter 100 has a male threaded end 120 that has a smaller cross-sectional diameter than the cylindrical mounting portion 140. Another aspect of the first end of the nail adapter 100 is a joint rod seat 110. The joint rod seat 110 is formed at the first end opening 105 of the nail adapter 100 and receives the flange 210 found on the coupler rod 200. The first end opening 105 also preferably has two alignment slots of varying width 112, 114. The alignment slots 112, 114 are preferably one hundred and eighty-degrees apart and are formed generally in the joint rod seat 110. The nail adapter 100 preferably has a tapered portion 165 between its first and second ends. The second end 160 of the nail adapter 100 has a smaller diameter than the cylindrical mounting portion 140, which is preferably the same outer diameter as the selected IMN 10. As is known to the industry, the second end 160 of the nail adapter 100 can also have intermittently spaced circumferential depth indicator grooves (not shown) that are capable of providing visible indication of the depth of a given IMN relative to its implanted position in the affected medullary canal of a patients bone. Further, the cylindrical mounting portion 140 of the first end of the nail adapter 100 is designed to receive the mounting collar 440 of the bridge adapter 400. Further, the beginning of the second end of the nail adapter 100 may include various configurations of tool receiving areas (not shown) that can be used to facilitate secure attachment of the coupler rod 200, the nail adapter 100, and a given IMN 10 respectively in a secure and unified manner.

Further, the nail adapter 100 can be configured with one or more depressions 130 that can be located along the length of the cylindrical mounting portion 140. Such depressions 130 can be useful for attaching elements used, for example, in facilitating IMN assembly and insertion. However, it is important that any added depressions do not interfere with the distal targeting capabilities of the targeting arm assembly.

Figure 4:
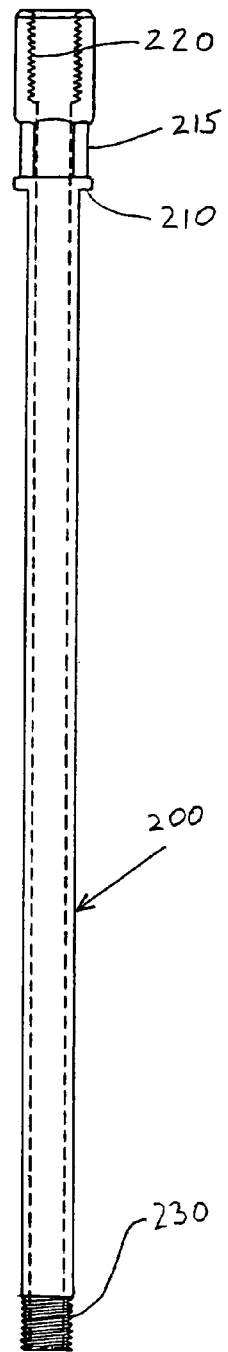
FIG. 4 shows the cannular coupler rod in accordance with an embodiment of the current invention.

FIG. 4 shows the cannular coupler rod 200 in accordance with a preferred embodiment of this invention. The coupler rod 200 has female threading 220 on the proximal inside cannular portion. Additionally, the first end of the coupler rod 200 preferably has a flange 210 design to mate with the joint rod set seat 110 of the nail adapter 100. Further, the first end of the coupler rod 200 has a tool mounting surface 215 that receives tools, such as wrenches. The second end of the coupler rod 200 has male threading 230.

Figure 5:
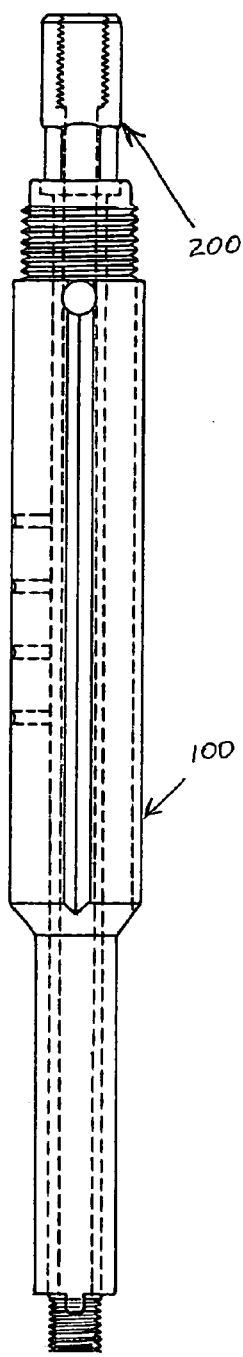
FIG. 5 shows a coupler rod inserted into and fully seated in a nail adapter in accordance with an embodiment of the current invention.
Figure 3F:
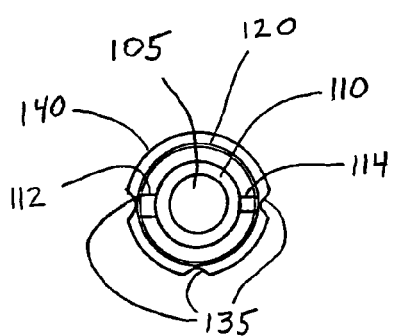

FIG. 5 shows the coupler rod 200 inserted into and fully seated in a nail adapter 100. The penetration of the coupler rod 200 through nail adapter 100 is limited by the engagement of the flange 210 and the joint rod seat 110. In the fully seated position shown in FIG. 5, the male threading 230 of the coupler rod 200 should preferably protrude beyond the second end of the nail adapter 100 for coupling with an IMN 10. It should be noted, however, that the overall length of both nail adapter 100 and the coupler rod 200 can be manufactured longer or shorter than those lengths shown, although the respective length of those two elements should correspond to take advantage of the coupling features discussed above.

Figure 22:
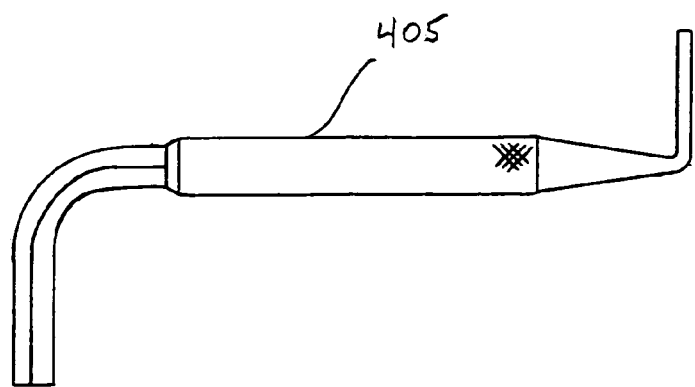
FIG. 22 shows a combination position pin and wrench in accordance with an embodiment of the current invention.

FIGS. 6a-d show a bridge adapter 400 in accordance with the present invention. The Bridge Adapter 400 is preferably configured for targeting as broad a range of proximal and distal targeting holes as possible in an attempt to facilitate a more universal targeting of IMN's. The bridge adapter 400 preferably has at its first end a cylindrical mounting collar 440 that preferably fits snuggly onto the cylindrical mounting portion 140 of the nail adapter 100. The mounting collar 440 can include one or more position windows 410, that when aligned can reveal the visible position numbers 149 inscribed or labeled on the cylindrical mounting portion 140 of the Nail Adapter 100 and labeling the transverse targeting position bores 141, 142, 143, and 144. By aligning one of the position numbers 149 within a window 410 a desired axial mounting position along the nail adapter 100 can be selected, which are preferably used for proximal locking. This can be additionally facilitated by using an alignment line 411 which is preferably provided. Further, in order to ensure a precise axial position along the longitudinal axis of the nail adapter 100, position pin holes 413 are provided. Once a position number 149 is properly aligned in a window 410, a position pin 405, as shown in FIG. 22, can be inserted through a position pin-hole 413 and into one of the targeting position bores 141, 142, 143, and 144 that correspond with the selected position. Alternatively, a spring loaded pin can be made integral to the bridge adapter 400 so as to potentially eliminate the need of a separate position pin.

The cylindrical mounting surface 140 of the nail adapter 100 and the mounting collar 440 preferably allow variations in the relative rotational and axial positions of the two adapters 100, 400. Once mounted, the bridge adapter 400 can be rotated three hundred and sixty-degree around the nail adapter 100. Also, the bridge adapter 400 is capable of multidirectional travel along the longitudinal axis of the nail adapter 100. Preferably, numerous screw holes 420, 422, 424 are provided in the mounting collar 440 to ensure it is secured in the desired location and configuration. A fixing screw 32 is used to selectively secure the mounting collar 440, and thus the entire bridge adapter 400 relative to the nail adapter 100. It is preferable that one or more fixing screws 32 be placed in non-intrusive screw holes 420, 422, 424 dependant upon the physical restrictions or environment in which the overall assembly is being used.

Figure 6B:
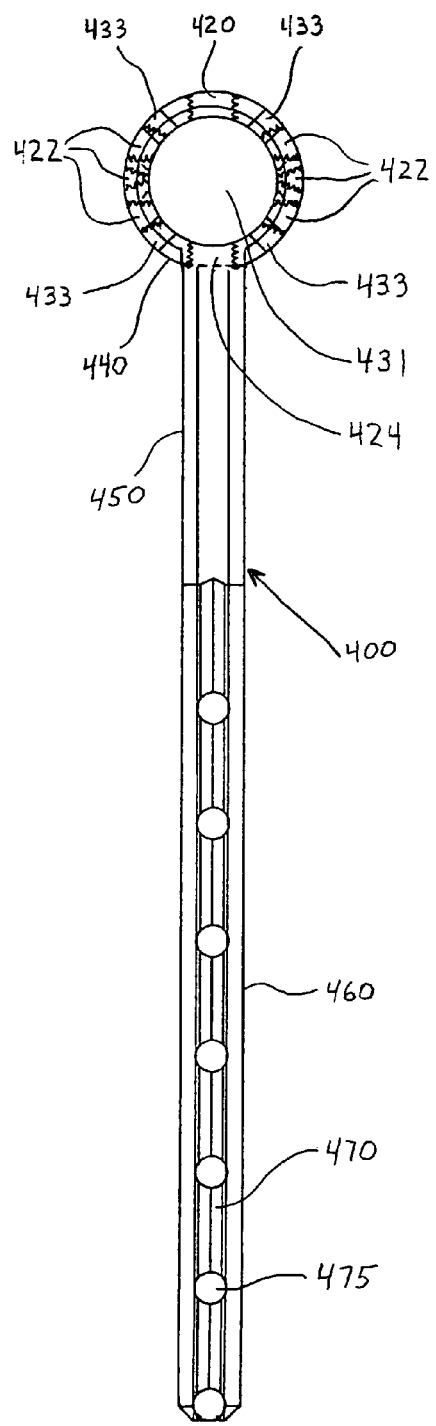
FIGS. 6a-d show plan, left side, bottom and top views, respectively, of a bridge adapter in accordance with an embodiment of the current invention.
Figure 6A:
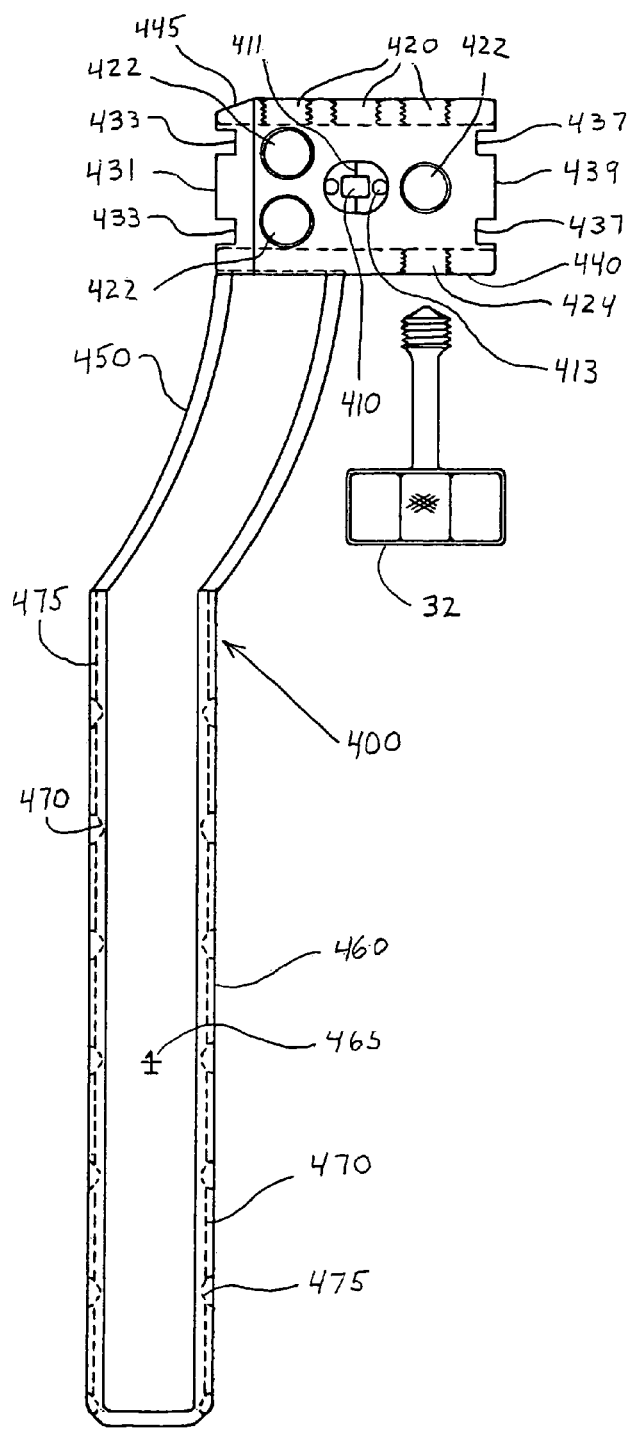

As the preferred embodiment of the present invention is a system intended to be applied during a surgical procedure, it can be beneficial to ensure that the various corners and edges of all the elements disclosed herein are not sharp or abrasive, except were indicated to be necessary. Thus as seen in FIG. 6a, the mounting collar 440 preferably includes a beveled edge 445 to suit this purpose. Additionally, the beveled edge 445 can make room or compensate for anatomical features of a patient that are in the region of the assembly. Similarly, the edge on the opposite side 439 could be provided with such a bevel (shown in the alternate embodiment of the mounting collar 440 seen in FIG. 1). Further, the present system and method is left/right indicated.

FIGS. 6a-d also show that the bridge adapter 400 preferably has a curved middle section 450 that connects the mounting collar 440 to a mounting shaft 460. When mounted, the length of the bridge adapter 400 generally extends away from the central longitudinal axis of the nail adapter 100. Also, the middle section 450 preferably extends radially outward from the central longitudinal axis of the nail adapter 100. In this way, the middle section 450 provides an axial offset to the mounting shaft 460 relative to the mounting collar 440. Thus, the central longitudinal axis of the mounting shaft 460 lies in a different position from the center of the mounting collar 440 relative to the longitudinal axis of the nail adapter 100. Also, the mounting collar 440, and the overall bridge adapter 400, can be assembled onto the nail adapter 100 in the opposite direction from that shown in FIG. 1. Thus, reversing the bridge adapter 400 could make the center of the mounting collar 440 lie closer to the IMN 10 than the mounting shaft 460 (this reversed configuration is not shown). The ability of the bridge adapter 400 to be selectively flipped and engaged onto the nail adapter 100 enhances the range of adjustment of the bridge adapter 400 relative the nail adapter 100 along its longitudinal axis. It should be noted that although the middle section 450 is shown to be curved in the preferred embodiment, it could be linear, stepped or any number of other shapes that provide the offset discussed above. Also, in yet another alternative embodiment, middle section 450 need not provide any offset and could be in-line with the center of the mounting shaft 460 portion of the bridge adapter 400.

Figure 6C:
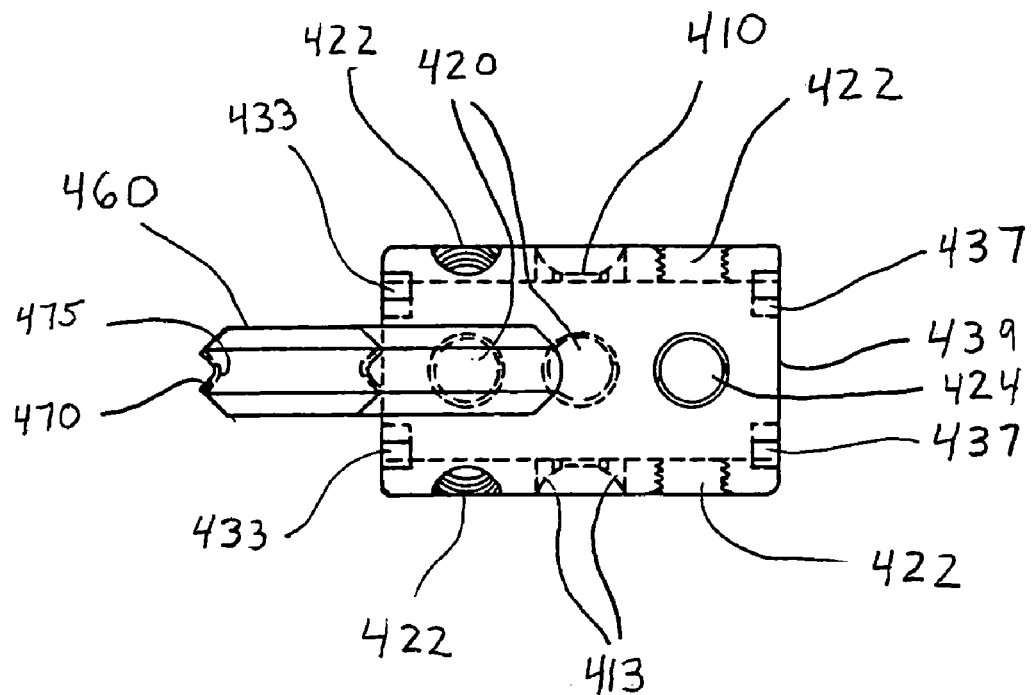
Figure 6D:
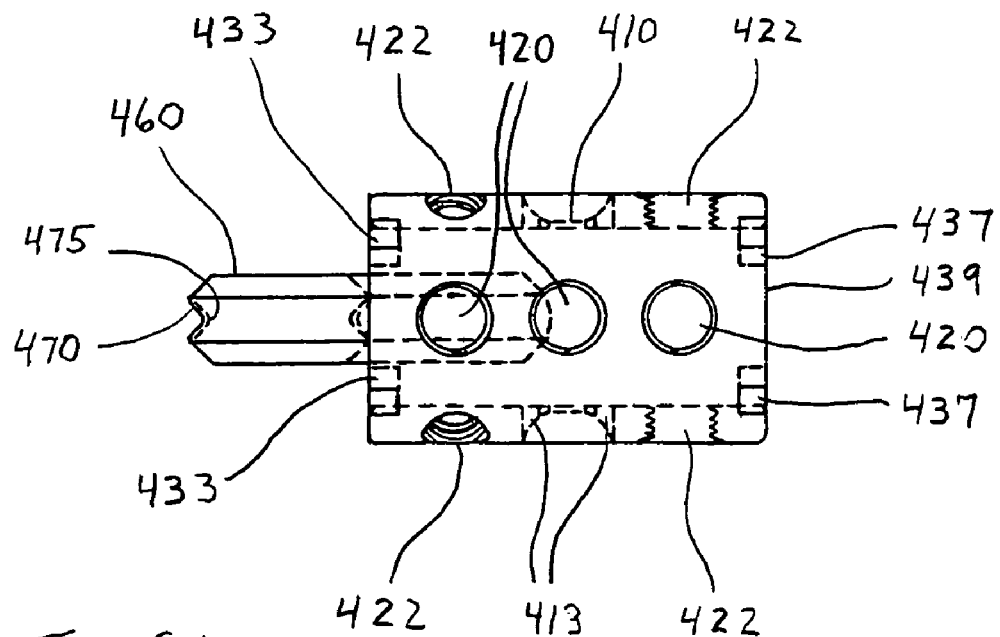
Figure 7B:
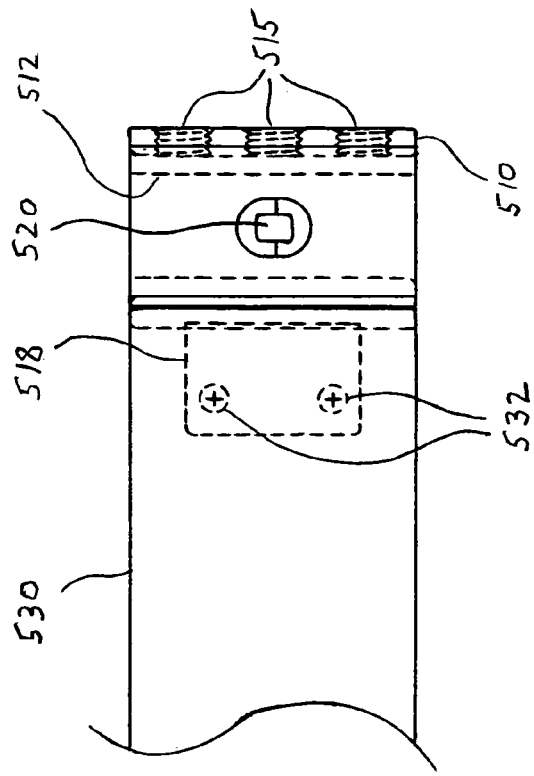
FIGS. 7a-d show plan, top, right side and left side views, respectively, of a targeting arm in accordance with an embodiment of the current invention.
Figure 7B:
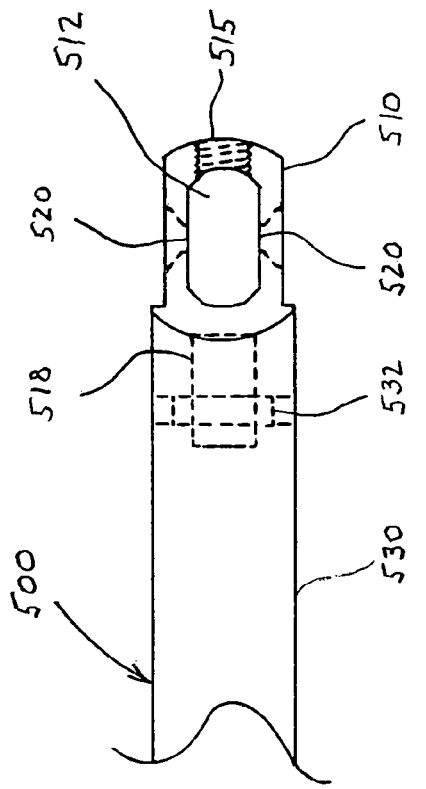
Figure 7A:
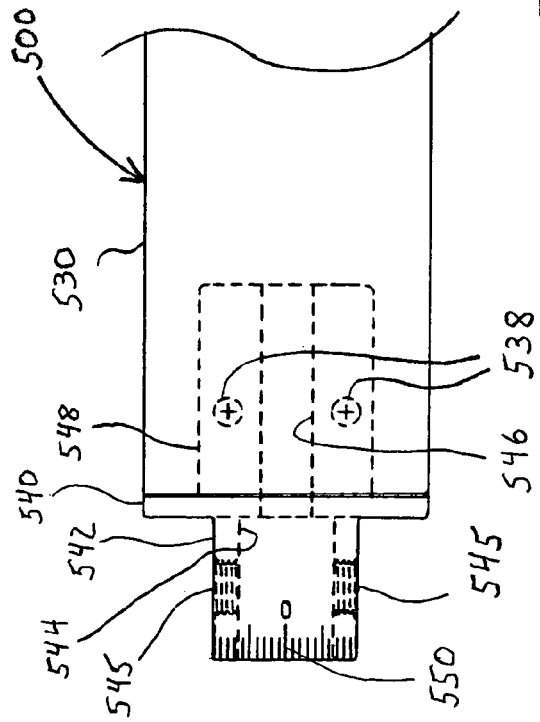
Figure 7A:
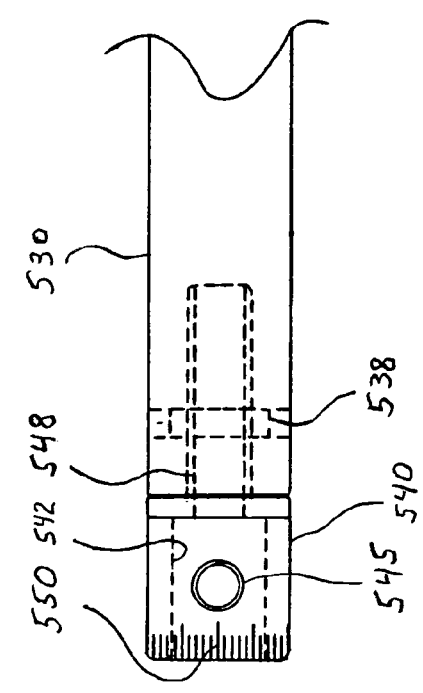
Figure 7D:
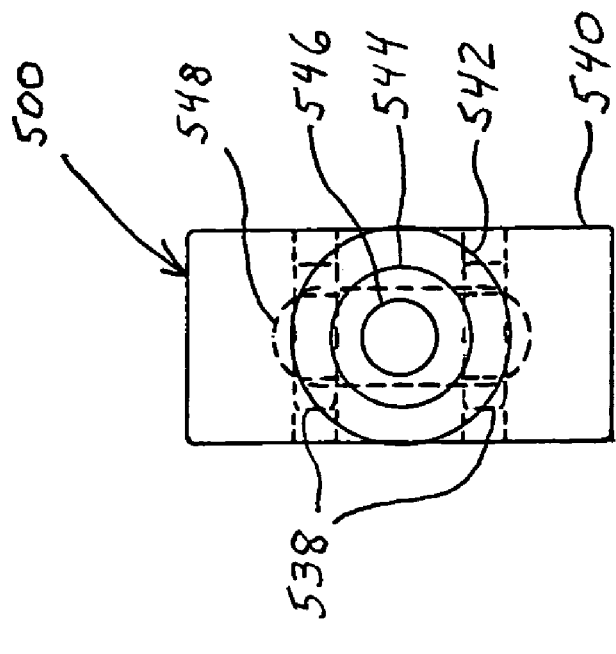
Figure 7C:
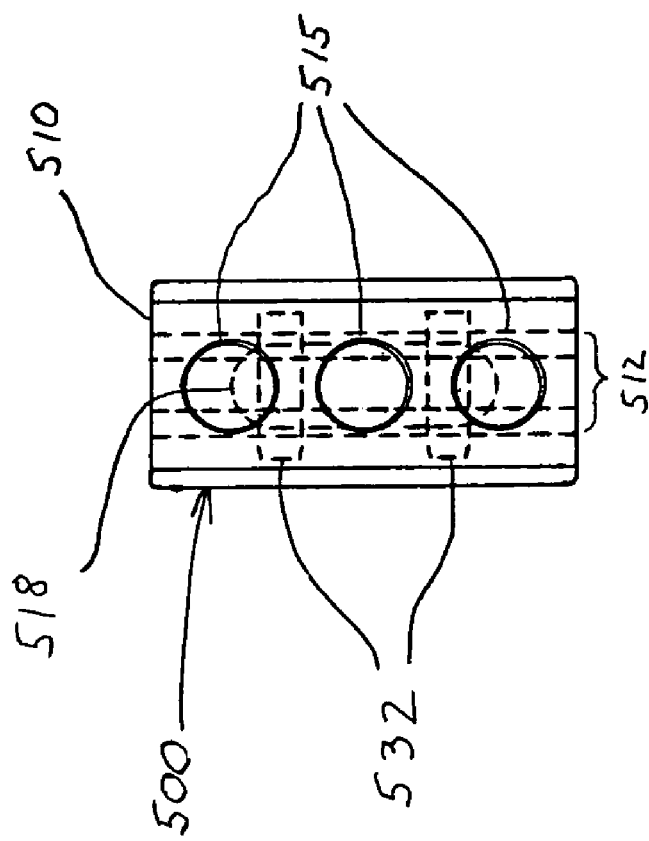

As seen more particularly in FIGS. 6c and 6d, the mounting shaft 460 preferably has a cross-section with two longer straight sides and two shorter convex sides. As further seen in FIGS. 6a-d, fixing screw grooves 470 are preferably included along the center of both shorter convex sides of the mounting shaft 460. Also, intermittently spaced along the fixing screw grooves 470 fixing screw recesses 475 are preferably provided. These fixing screw recesses 475 are preferably made to receive yet another fixing screw 34 discussed further below with regard to the targeting arm 500. Additionally, along the two longer straight sides of the mounting shaft 460, are preferably one or more evenly spaced inscribed or labeled numeric position indicators 465. A multitude of numeric indicators 465 can be provided, which serve a similar purpose to the position numbers 149 discussed above. However, here the numeric indicators 465 are used with respect to the bridge adapter 400 and the targeting arm 500. The bridge adapter 400 once mounted preferably does not obstruct access to the inner cannular portions of the extension rod 200 or the IMN 100.

FIGS. 7a-d show a distal targeting arm 500 in accordance with the preferred embodiment of the present invention. The first end of the distal targeting arm 500 preferably includes a generally oblong mounting collar 510 that fits snugly onto the mounting shaft 460 of the bridge adapter 400. Thus, the inner aperture 512 of the oblong mounting collar 510 should match the cross-sectional characteristics of the mounting shaft 460. Preferably, mounting collar 510 is reversibly mounted onto the mounting shaft 460, but either orientation should maintain the final assembled state of the distal targeting arm 500 parallel to the longitudinal axis of the nail adapter 100. It should be noted that IMN's are often manufactured with varying curves and/or bends. Further, an IMN can deform when implanted into a given patients intramedullary canal. Therefore, the assembled targeting arm (whether a distal or proximal arm) is not necessarily parallel to the implanted IMN to which it is coupled. Rather, the given targeting arm is generally parallel to the assembled nail adapter 100. Additionally, the oblong mounting collar 510 preferably includes one or more fixing screw holes 515 made to receive a fixing screw 34 and selectively secure the oblong mounting collar 510 and thus the entire distal targeting arm 500 relative to the bridge adapter 400. In an assembled state, once a fixing screw 34 is engaged in the fixing screw hole 515, the fixing screw 34 is preferably seated in fixing screw recesses 475 of the bridge adapter 400. Although, the screw could also rest in the fixing screw grooves 470 of the bridge adapter 400.

The oblong mounting collar 510 preferably also includes at least one position window 520 similar to the window 410 discussed above for the mounting collar 440 on the bridge adapter 400. Further, the oblong mounting collar preferably includes an integral first protruding connector 518 which is designed to mate with other elements of the invention. In particular, in the preferred embodiment, the first protruding connector 518 should mate with the corresponding recess in the distal targeting arm body 530. Thus, once assembled, the targeting arm body 530 and the oblong mounting collar 510 can be fastened together using fasteners 532. It is also preferable that fasteners 532 lie beneath the surface of the targeting arm body 530 and are plugged leaving a finished smooth outer surface on the body 530. When the distal targeting arm body 530 is assembled with the oblong mounting collar 510 onto the bridge adapter 400, the central longitudinal axis of the distal targeting arm body 530 should extend generally parallel to the central longitudinal axis of the nail adapter 100. Additionally, the targeting arm body 530 is preferably constructed from a durable lightweight artifact free radial lucent material, such as carbon fiber laminate, that is specifically constructed to be rigid and resistant to torsional forces.

FIGS. 7a-d also show the second end of the targeting arm 500, which includes a mounting extension 540. The mounting extension 540 preferably also includes a cylindrical protruding portion 542. This cylindrical protruding portion 542 preferably includes a first cylindrical receiving aperture 544 and a second cylindrical receiving aperture 546 which is located in the second protruding connector 548. Thus, when assembled the second protruding connector should be mated with the target arm body and affixed with fasteners 538. As with fasteners 532 above, fasteners 538 are preferably plugged after being secured in order to leave a smooth outer finish on the body 530. Additionally, the cylindrical protruding portion 542 preferably includes at least one fixing screw hole 545 and calibration markings 550.

It may be advantageous to create a variety of such distal targeting arms 500 of varying length (for example, 8, 10, and 12 inches long measured along the mid-section). As the system of this invention is modular, multiple targeting arms of varied length would provide a greater range of flexibility within the system by allowing the most ideal sized arm to be exploited in a given situation. Interchangeable targeting arms also compensate for the great variety in lengths of IMN's presently on the market. It is also understood that a distal targeting arm is capable of being made to be telescopic (capable of extension and retraction) so that the capabilities of varying lengths of distal targeting arms are exploited in a single arm.

Figure 8B:
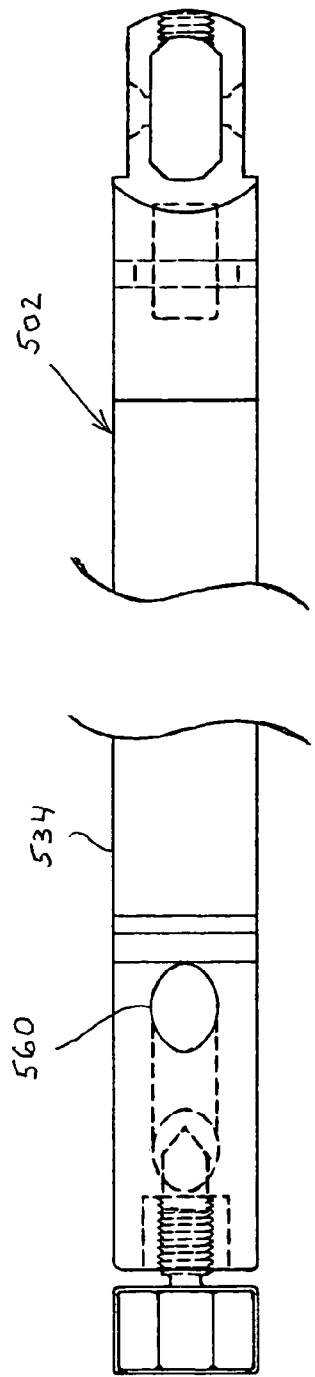
Figure 9B:
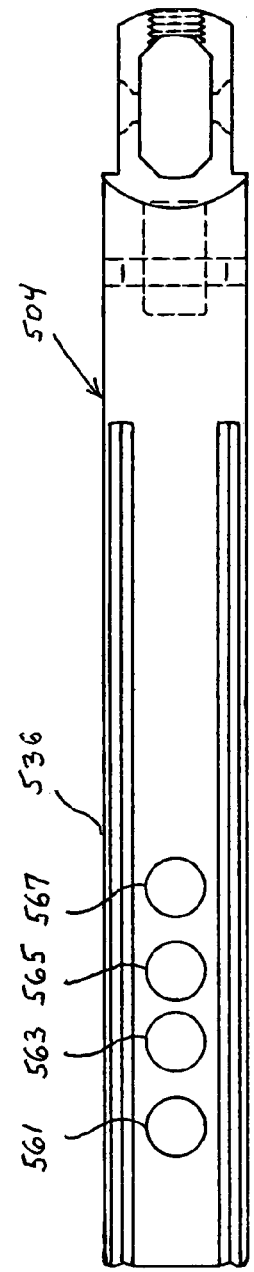

Alternatively, FIGS. 8a-b and 9a-b show two additional embodiments of exemplary proximal targeting arms 502, 504. These alternate embodiments primarily show variations in proximal targeting arm bodies 534, 536 which incorporate some of the features of the targeting head 700 discussed below. The proximal side of these arms (as seen on the right in the FIGS. 8 a-b and 9 a-b) is preferably similar to that of distal targeting arm 500. Also, FIGS. 8a-b show a proximal targeting arm 502 capable of targeting an oblique (angled) proximal hole/position. The present system can exploit various proximal targeting arms that can potentially target most existing and/or conceived oblique proximal locking position/hole. They can be of varying dimensions and lengths as well. The "diagonal" (oblique) slot 560 is an exemplary oblique (angled) target trajectory hole/bore that is used for angled proximal targeting as is common in the industry. The small v-groove 570 allows the arm to accept a trocar locking element that has a collar at its first end that could rest in the v-groove. The trocar can among other things act as the drill sleeve/guide.

FIGS. 9 a-b show a proximal targeting arm 504 intended for transverse proximal targeting. One or more targeting slot(s) 561, 563, 565, 567 can be provided for targeting, similar to slot 560 above but not at an angle. Some elements of contemplated/exemplary proximal targeting arms (for instance, oblong mounting collar, targeting arm body . . . ) will have some basic construction similarities to those of the previously mentioned distal targeting arm.

Figure 10A:
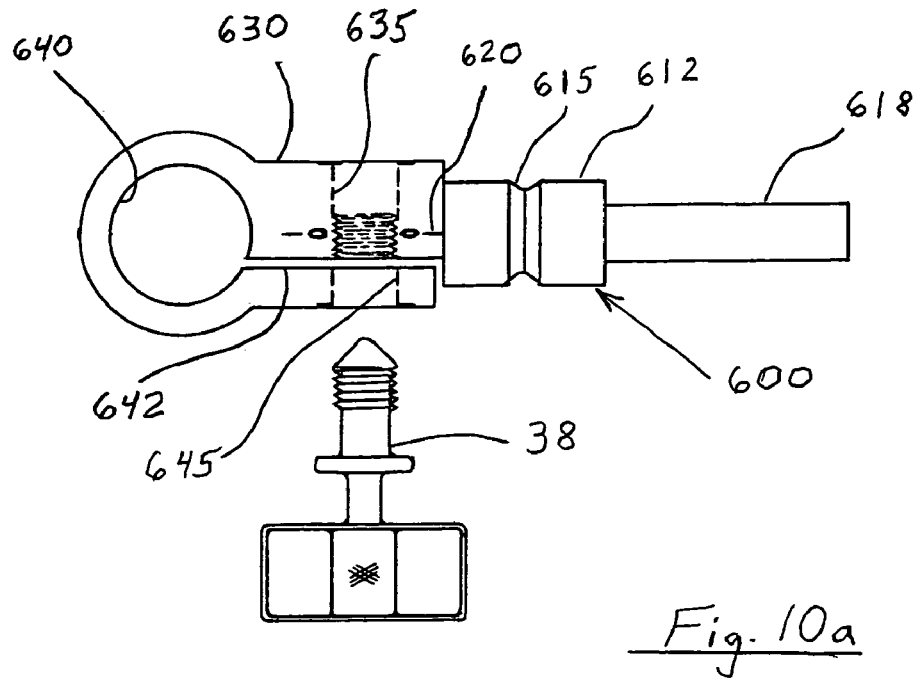
FIGS. 10a-c show plan, top and right side views, respectively, of a head coupling in accordance with an embodiment of the current invention.
Figure 10B:
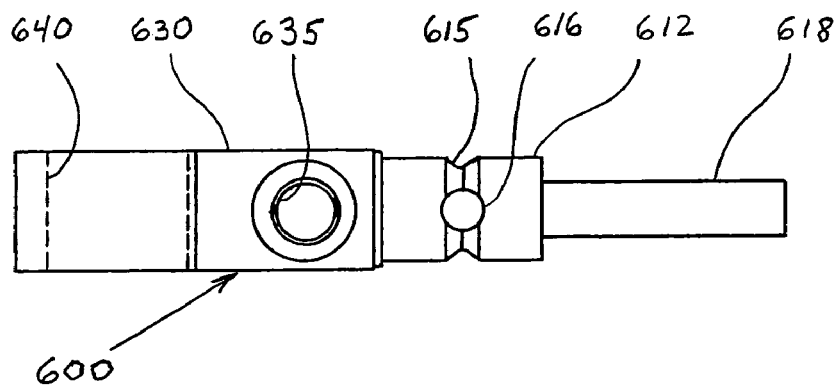
Figure 10C:
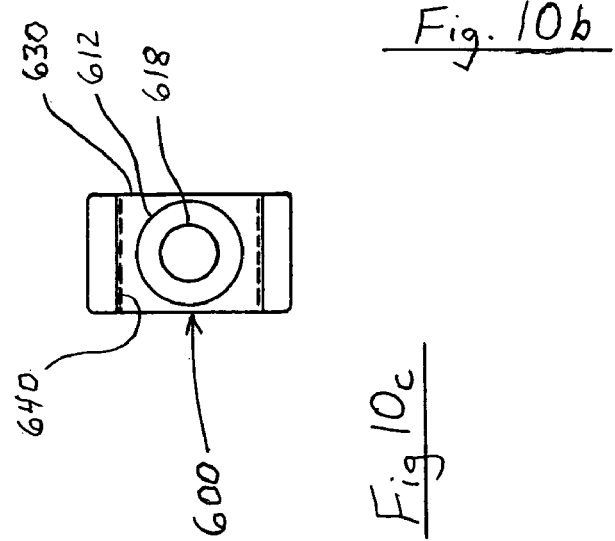

FIGS. 10a-c show a head coupling 600 in accordance with the preferred embodiment of the present invention. The head coupling 600 preferably includes a cylindrical mating portion 612 which includes a fixing screw groove 615 thereon. Additionally, the cylindrical mating portion 612 preferably includes a fixing screw seat 616, as seen in FIG. 10b. Further, a mating post 618 together with the cylindrical mating portion 612 are preferably designed to fit within the first and second cylindrical receiving apertures 544, 546 on the mounting extension 540. In an assembled state, a fixing screw or optional Allen wrench set screw (not shown) is preferably inserted into fixing screw hole 545 and into either the fixing screw groove 615 or preferably the fixing screw seat 616. The head coupling body 630 includes rotational calibration markings 620 which when assembled should preferably line up with the calibration indicators 550 on the mounting extension 540. The zero position for the calibration indicators 550 preferably corresponds to a configuration when the fixing screw seat 616 is engaged by the fixing screw. Thus, the fixed position of the head coupling 600 can be rotationally adjusted relative to the target arm 500 and the longitudinal axis they preferably share. Further, the head coupling body 630, which is integrally attached to the cylindrical mating portion 612, preferably includes a split ring portion 640 designed to mate with features of the targeting head 700. As particularly seen in FIG. 10a, the split ring portion 640 has an extension tab 642. Thus, the head coupling 600 acts like a clasp when the targeting head 700 cylindrical mounting post 720 is inserted in the split ring portion 640 and tightened with the fixing screw 38. In an assembled configuration, a fixing screw 38 can be inserted through a first cylindrically smooth fixing screw hole 645 and into a second partially female threaded fixing screw hole 635. In this way the fixing screw will tighten and/or close the split ring portion 640 when the fixing screw 38 is tightened. Preferably, the split ring portion 640 is intended to receive and mate with a post 720 on the targeting head 700.

Figure 11B:
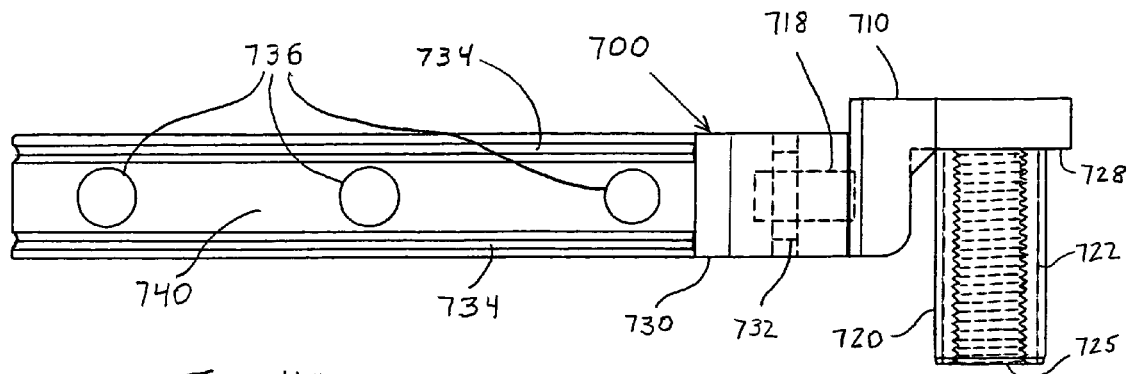
FIGS. 11a-c show plan, bottom and back views, respectively, of a targeting head in accordance with an embodiment of the current invention.
Figure 11C:
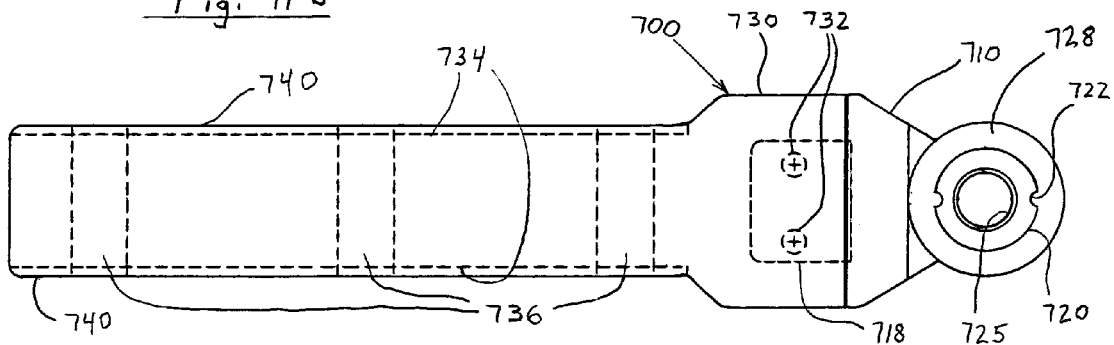
Figure 11A:
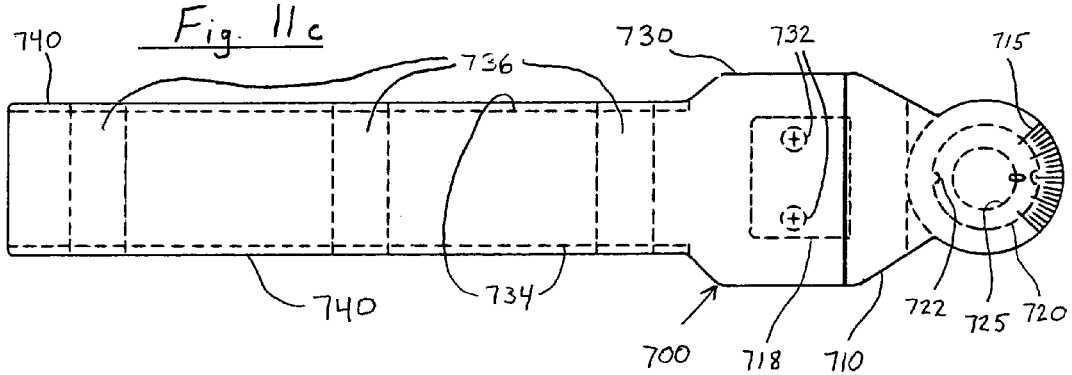

FIGS. 11a-c show a distal targeting head 700 in accordance with the preferred embodiments of the present invention. The targeting head 700 preferably includes a mounting portion 710 that has a cylindrical mounting post 720. The mounting post 720 includes a female threaded hollow portion 725 designed to receive a calibration accessory used to gauge relocation progress of the assembly as targeting takes place. This is similar to calibration markings 715 in that in can be used to view changes in position of the targeting head relative to its position in the head coupling 600. When mounted, the head coupling 600 can rest against the head coupling seat 728 on the mounting portion 710 of the targeting head 700. However, in some circumstances, certain IMN's and IMN deflection may not enable a full seating. Additionally, the mounting post 720 includes at least one position groove 722. The position groove(s) 722 hold a calibration accessory (not shown) used to gauge relocation progress of the assembly as targeting takes place in a position relative to the mounting post 720 found on the targeting head 700 (as the mounting post turns the calibration accessory (not shown) can turn with it, thus providing visual indication from the underside of the targeting head 700 (similar to what the calibration markings 715 do from the top side). This can be beneficial as the distal targeting arm 500, the head coupling 600, and the distal targeting head 700 as a modular unit of the distal targeting assembly can be flipped on the mounting shaft 460 of the bridge adapter 400 by means of the mounting collar 510 found on the distal targeting arm 500. This flipping method quickly compensates for potential IMN deflection and subsequently exposes the underside of the distal targeting head 700 to the clinician. Thus, it is also important to have a means for gauging distal targeting head 700 movement from the underside position of the distal targeting head 700. Further, the mounting portion 710 preferably includes a protruding connector 718, which is intended to mate with the targeting head body 730. The targeting head body 730 is preferably constructed from a durable lightweight artifact-free, radial, translucent material, such as carbon fiber laminate, that is specifically constructed to be rigid and resistant to torsional forces. Once assembled, the mounting portion 710 and the targeting head body 730 are preferably secured with fasteners 732. Also, once assembled, the mounting portion 710 includes calibration markings 715 designed to align with the rotational calibration markings 620 on the coupling head 600.

The distal targeting head 700 can hold among other things, a target console 800, trocar or triple trocar (used as a drill guide, tissue protection sleeve and insertion point to introduce/advance sleeves until preferably making contact with affected bone) and trocar locking devices. Also, the distal targeting head 700 can have one or more target trajectory bores 736. Distal targeting head 700 can be of varying length. If one such common distal targeting technique is to be utilized (the perfect circle technique, using c-arm navigational viewing until perfect circles appear under image intensification) then a non-radiolucent (visible under image intensification) cross-hair would have to be positioned into the target trajectory bore integral with the distal targeting head.

Figure 12A:
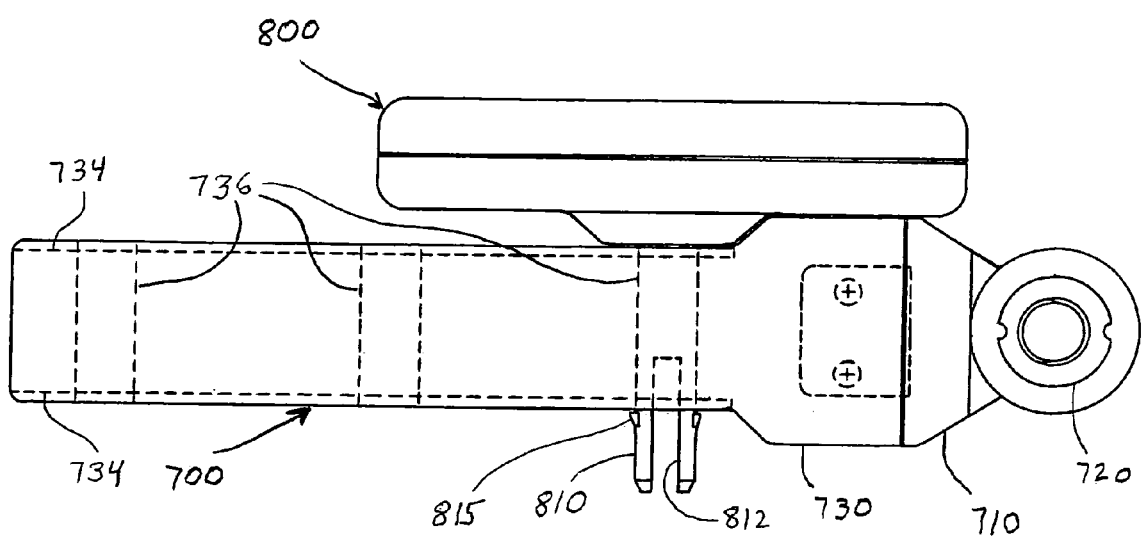
FIGS. 12a-b show plan and bottom views of a targeting console mounted on a targeting head in accordance with an embodiment of the current invention.
Figure 12B:
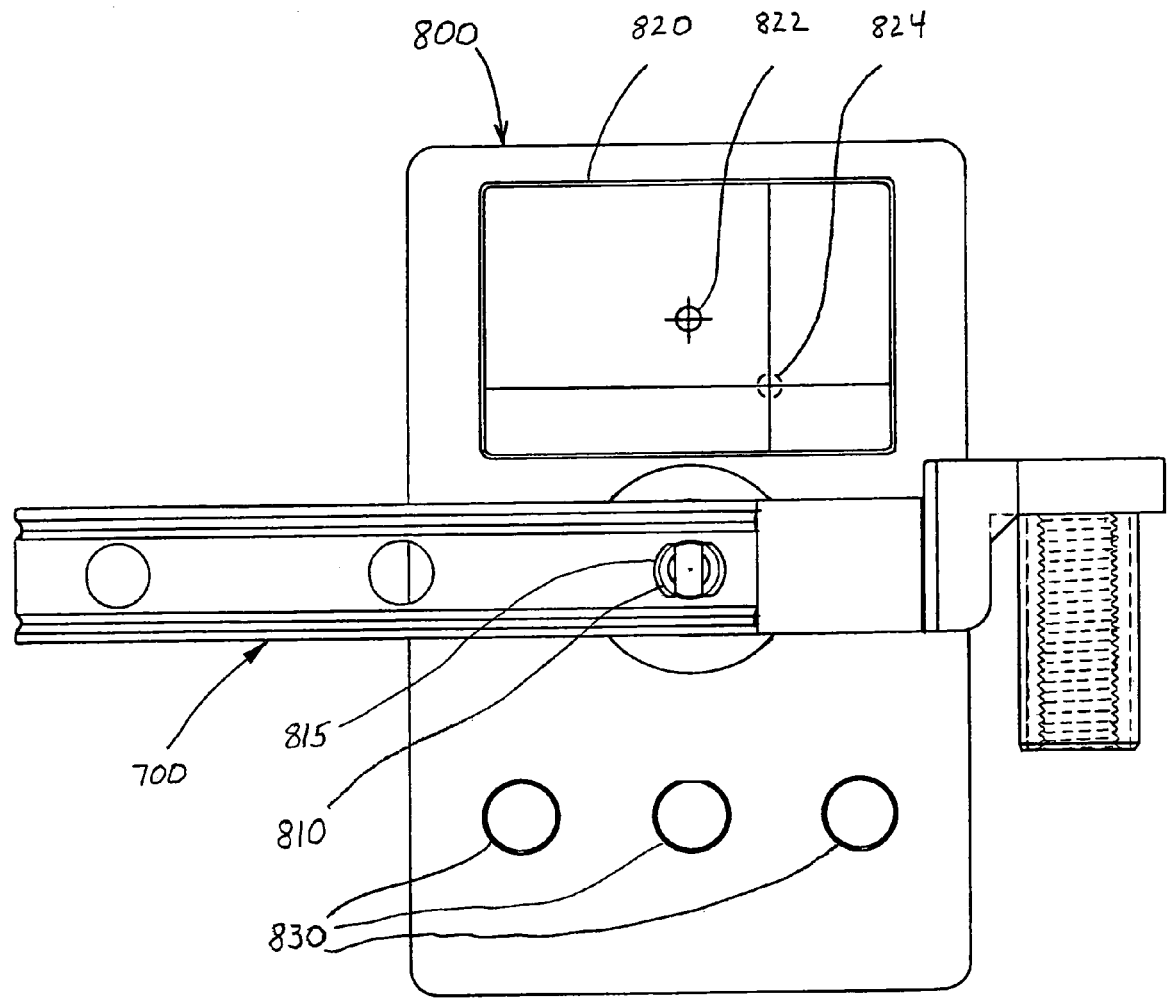

As seen in FIGS. 12a and 12b the targeting head 700 is intended to hold the targeting console 800. The distal targeting head 700 shown in FIGS. 11-12 includes multiple trajectory bores used for mounting the targeting console 800. Further, mounting grooves 734 and mounting holes 736 are provided to accommodate and hold more than one type of console attachment, or potentially other surgical accessories. Such accessories or equipment include, but are not limited to, drill sleeves, tissue-protection sleeves, trocars, trocar locking elements, drill bits, locking screws and screwdriver. It may be advantageous for the center of the console screen 820 and the center of the effective central axis of the integral console 800 to be centered on the effective central axis of the mounting holes 736 in the distal targeting head 700. Also, the targeting console 800 should preferably have a means for preventing rotation of the targeting console 800 while it is inserted in a mounting hole 736 of the distal targeting head 700. Further, the "mounting" grooves 734 are actually locking grooves that accept a trocar locking element. This element is used to prevent slippage (in or out) of the trocar once it is inserted into the mounting holes 736 in the distal targeting head 700. It should be noted that mounting holes 736 are also the distal targeting head's targeting trajectory bores. These bores 736 preferably hold, among other things, drilling equipment used in conjunction with the subject invention.

FIGS. 12a and 12b also show (a) an exemplary targeting console 800 mounted to the targeting head 700 with a quick connect mounting post 810. Preferably, such a mounting post 810 includes flexible post extensions 812 which combined with the locking tabs 815 can engage the operative side of the targeting head 700 when the mounting post 810 is fully inserted in the mounting holes 736. By squeezing the flexible post extensions 815 the locking tabs will disengage the outer surface 740 of the targeting head 700, and thus the targeting console 800 can be removed. Console 800 also preferably includes but is not limited to the following, a targeting display 820 and power, reset/null, and selector switch controls 830, as seen in FIG. 12b. It is understood that the reset/null function can be a built in automatic function as well.

The targeting console 800 preferably has an array of integral magnetic field sensor elements disposed in known locations relative to the console's effective central axis. Thus, a targeting sensor comprising a portion capable of generating magnetic field values corresponding to its three dimensional location and orientation can be inserted in an IMN 10. The targeting sensor 905 preferably generates a magnetic field adapted to identify its position and at least two points of orientation within the IMN 10. Once the effective axis of the desired guide hole 736 in the distal targeting head 700 has been aligned, by means of the tandemly coupled targeting console 800 with the effective central axis of the sensor 905, the distally targeted position is considered to be located or identified. The internal targeting console 800 array's magnetic field sensor elements detect and monitor the targeting sensor's magnet field. The targeting console's 800 onboard systems process sensor data and determine any misalignment between the effective central axis of the console or another relative position, and the effective central axis of the target sensor. The targeting console 800 display screen 820 provides a visual indication of any misalignment between a select guide hole 736 and the central axis of the target sensor (not shown). In the exemplary console screen, the central crosshairs 822 preferably represent the effective central axis of the targeting console 800. Further, the cross-lined indicator 824 preferably represents the current relative location of the target sensor, or the relative location of where it ultimately needs to be to align the distal target trajectory bores 736 with the targeted distal receiving bore(s) 13, 15 found in the exemplary IMN in FIG. 2. This provides clinicians with responsive interaction and updated localization of the central axis of the target relative to the central axis of the drill guide 830. The targeting console 800 is preferably lightweight compact, self-contained and self-powered. It is understood that power sources such as batteries can interfere with sensor output, therefore a remote, shielded or partitioned power-supply may be exploited in the present system.

The assembly described above can be used to secure solid IMN's that include an embedded target sensor. The exact relative positions of the distal target holes, such as the receiving bores 13, 15 shown in FIG. 2, are preferably known so that the targeting console 800 can be configured to properly align at least one target trajectory hole 736 found in the distal targeting head 700 with at least one such distal locking hole 13, 15.

It is understood that the present system and method can exploit and incorporate various Computer-Assisted Surgery (CAS) techniques that are currently used in visualizing locking screw target locations. Such techniques include magnetic, optical or infrared systems. Examples of such systems are the Polaris® and Optotrack® (by Northern Digital, Inc., Ontario, Canada). Additionally, other such systems are disclosed in U.S. Pat. No. 5,411,503 to Hollstien et al., May 2, 1995, titled "Instrumentation for Distal Targeting of Locking Screws in Intramedullary Nails,"; U.S. Patent Application Publication US 2005/0049820 A1, entitled "Gain Factor and Position Determination System", filed Jul. 22, 2003; U.S. Patent Application Publication US 2004/0088136 A1, entitled "Method Of Measuring Position And Orientation With Improved Signal To Noise Ratio", filed Nov. 1, 2002; U.S. Patent Application Publication US 2005/0075562 A1, entitled "Magnetic Targeting Device," filed Apr. 7, 2005; U.S. Patent Application Publication US 2004/001365 A1, entitled "Medical Sensor Having Power Coil Sensing Coil and Control Chip", filed Jan. 22, 2004; U.S. Patent Application Publication US 2004/0034355 A1, entitled "Distal Targeting of Locking Screws in Intramedullary Nails", filed Feb. 19, 2004; and U.S. Patent Application Publication US 2005/0080427 A1, also entitled "Distal Targeting of Locking Screws in Intramedullary Nails", filed Apr. 14, 2005, all of which disclosures are hereby incorporated by reference. Other techniques include Image-Guided Surgery techniques (IGS), such as phantom-based image/anatomy registration; virtual fluoroscopy using infrared signals; stereo fluoroscopy; laser-guided systems, sound-guided systems (i.e., ultrasound); Computed-tomography (CT); or combined CT and fluoroscopy techniques; robot assisted IMN devices; mechanical devices such as an adapted gimbal mounted magnaprobe; and the like. It is understood that the present system and method can alternatively exploit and incorporate any of these techniques and others not mentioned and that such techniques can facilitate the location of one or more locking positions such as a locking hole found in a given manufacturers IMN when used in conjunction with the present system.

Alternatively, if a cannular IMN is used that does not include a pre-embedded target sensor, then the target sensor probe of the present invention can be used. Once the assembly shown in FIG. 1 is completed, the target sensor probe assembly 900, shown in FIGS. 15*a-c*, can preferably be mounted on the end of both the nail adaptor 100 and the coupler rod 200. The target sensor probe assembly 900 is preferably used to insert the target sensor 905 into the IMN 10. Such a target sensor 905 can be made from, for example, a neodymium magnet (Nd—Fe—B). Such magnets are preferably diametrically magnetized, thus defining opposed poles and a central axis as mentioned above.

The target sensor probe assembly is preferably used to deliver the target sensor 905, which is used to more precisely locate the position and orientation of the targeted distal receiving bores 13, 15 in the IMN 10. In one embodiment, the sensor is placed directly in the center of the longitudinal position of a particular receiving bore 13, 15 for targeting. Preferably, the most distal of the targeted receiving bores is lined-up first and then the more proximal targeted receiving bores are targeted afterwards. However, the present system can also be configured so that it is possible to offset the target sensor in the proximal direction in a known location/orientation relative to a targeted locking position in an IMN 10. Such an offset configuration could eliminate the need to advance the target sensor prior to interlocking additional receiving bores. This can also be used in the pre-embedded IMN where the sensor can't be embedded in opening of the distal locking hole in a given IMN due to the need to drill/lock the hole.

FIGS. 13-19 show various features of the target sensor probe assembly 900. In particular, FIGS. 13*a-c* show the preferred inner parts or subassembly of the target sensor probe assembly 900 before they are assembled in the probe cylinder 960. It should be noted that one particular advantage of the present invention is that it can accommodate the use of either a wired or wireless target sensor. The cannular features of the nail adapter 100, the coupler rod 200, and other proximal elements can accommodate a continuous wire connecting the target sensor 905 and the targeting console 800.

A target sensor 905 is preferably coupled to one end of an extension rod 910 through a frictional compression fit. Similarly, the mating end 907 of the target sensor 905 is preferably compression fit into the distal mating end 912 of the extension rod 910. In order to eliminate relative rotation between the mating members at these joints, a non-circular cross-section is provided for the mating ends. The proximal mating end 918 of the extension rod 910 is then preferably coupled to the distal end of the probe rod 920. However, the male-female coupling configuration shown in the lower part of FIG. 13*a* can be interchanged such that the parts which show a female receiving bore could potentially have a male tab and visa-versa. Additionally, in an alternative embodiment, the coupling configuration could be altered to allow the optional use of extension rod 910, thus coupling the target sensor 905 directly to probe 920. In this way, extension rod 910 could be used only when needed for added length to reach the distal end of the target location. In a further alternative embodiment, the diameter of the distal portion of probe rod 920 could be reduced to maintain a continuous transitional diameter between probe rod 920 and extension rod 910. Regardless of the coupling configuration, it is preferred that the probe rod 920 and extension rod 910 be made of strong and flexible materials, such as high density polyethylene (HDPE). Also, it is preferred that this assembly be modular, so that any individual piece can be easily replaced.

The probe rod 920 is preferably used to insert the target sensor 905 through the other cannular element, such as the nail adaptor 100, the coupler rod 200 and the IMN 10 to a pre-determined distal target. Thus, the probe rod 920 is provided with a handle 925 to assist in this regard. Preferably, the target sensor probe assembly 900 is provided with a spring mechanism that comprises a spring 940 that is supported at the distal end by a spring base washer 930 and supported at the proximal end by a guide washer 950. It should be noted however, that the guide washer 950 is preferably configured to be fixed relative to the axial movement of the probe rod 920, as opposed to the spring base washer, which is allowed axial movement within limitations. The guide washer 950 is generally held in place by two retaining clips 952, 958, which hold the guide washer in place with respect to the probe rod 920. Additionally, the guide washer is provided with position pins 955, which further guide the movement of the probe rod 920 through the probe cylinder 960. While the guide washer 950 generally maintains the probe rod 920 in a central longitudinal position within the probe cylinder 960, the position pins limit the movement of the rod to the guide and position slots 970, 975 in the probe cylinder 960. Thus, the position pins 955 also limit the relative distal targeting positions, as they control the probe rod 920, extension rod 910 and target sensor 905.

FIGS. 14a & 15a show the slots 970, 975 that pass completely through the wall of the probe cylinder 960. These slots 970, 975 that are shown are exemplary slots only. Preferably, such slots should coincide with a given IMN's distal locking hole(s)/position(s). The slot configuration is preferably configured to coincide with the distal locking hole(s)/position(s) found on the IMN with which it is intended to be used. A simplified sensor probe could be exploited where less demanding positioning is dictated. It is possible to make the present systems sensor probe adjustable so as to work with a range of IMN's of varying length. The distal end of the probe rod 920 and extension rod 910 can be provided with centering shims (not shown) similar to the position shim 995 found on the calibration probe (see FIG. 20). These probe centering shims facilitate the probe being centered in the cannular shaft of the IMN and locking hole positions. Although shim 995 is shown off-center in FIG. 20, the sensor probe shims (not shown) would preferably center the probe and/or extension rod(s).

Any deviation to original distance or rotation that is translated to a calibration probe may be adapted to the sensor delivery probe. A groove in the center of a locking position might aid in establishing rotational deformities. The probe as it engages with a locking position can be pulled back or manually retracted so as to insure engagement of the calibration probe with this center groove, thus establishing altered distance and any rotation deformation.

Figure 15B:
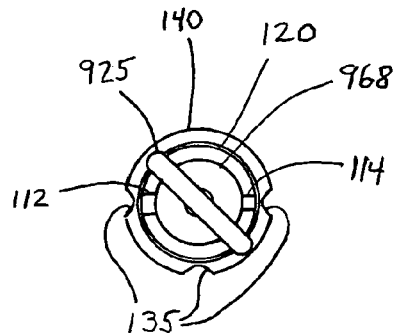
Figure 18:
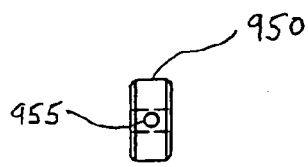
FIG. 18 shows a plan view of a guide washer in accordance with an embodiment of the current invention.
Figure 17:
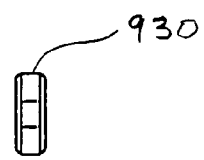
FIG. 17 shows a plan view of a spring base washer in accordance with an embodiment of the current invention.
Figure 19A:
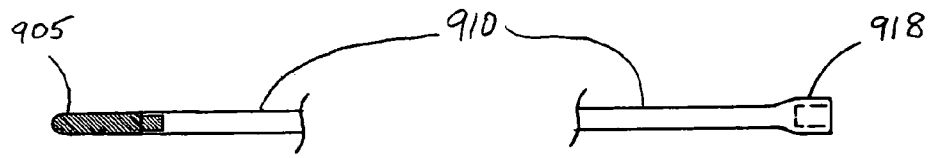
FIGS. 19a-c show plan, bottom and top views, respectively, of an extension rod in accordance with an embodiment of the current invention.
Figure 19B:
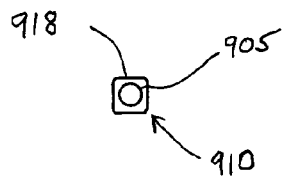
Figure 19C:

FIGS. 14a-c and 15a-b show the full target sensor probe assembly 900. Also, FIGS. 15a-b show the target sensor probe assembly 900 mounted onto the proximal end of the nail adaptor 100 and the coupler rod 200. In order for the target sensor probe assembly 900 to be fully assembled, prior to the installation of the spring mechanism 930, 940, 950 and the attachment to extension rod 910 (if applicable) a probe cylinder cap 968 should be inserted onto the probe rod 920 so that it rests near the handle 925 and can be used to close off the probe cylinder 960 in the final assembly.

Once the probe cylinder cap 968 is inserted onto the probe rod 920, the remaining assembly seen in FIG. 13a is inserted into the probe cylinder 960. Then, the probe cylinder cap 968 can be secured onto the top of the probe cylinder 960. The assembly could be built, the cap installed and the finger loop 925 completed (bent) after assembly. The probe cylinder 960 is provided with retention tabs 965, which extend radially inward and limit the movement of the spring base washer 930 within the probe cylinder 960. Also, the probe cylinder 960 is provided with longitudinal guide slots 970, which direct the movement of the position pins 955 through the probe cylinder 960. Also, position slots 975 branch off the guide slot 970. Thus, the rotational movement of the probe rod and its subassembly is limited to movement within the guide slots 970, 975.

As seen in FIGS. 14a and 15a, the position slots 975 shown are configured so that when a position pin 955 is seated in the proximal end of the position slot 975, the target sensor 905 (connected via the probe rod 920) is aligned with a pre-selected position relative to at least one receiving bore 13, 15 in the IMN 10. Actually, FIGS. 14a & 15a show various exemplary slot configurations which do not necessarily relate to the IMN 10 shown in FIG. 2. The connected spring assembly 930, 940, 950 helps bias the position pins 955 in the proximal direction helping them stay in the selected slot 975. Preferably, a position slot 975 is provided that places the target sensor in a position that corresponds with each available receiving bore 13, 15 in an intended nail having corresponding distal locking hole configurations as the target sensor probe. In the preferred embodiment, the slots 970, 975 pass completely through the wall of the probe cylinder 960. In this way, an external visible indication is provided of the current relative position of the target sensor 905. Additionally, by having the position pins 955 extend radially beyond the circumference of the probe cylinder 960, additional clamps can be employed (not shown) to further restrain the movement of the pins 955, and thus the target sensor 905. A self-tightening, spring-loaded, clamping mechanism, such as a modified Corbin clamp, could be employed for this purpose. This can facilitate targeting locking positions (for example static and dynamic locking positions) as well as locking holes. For instance, the middle slots seen in FIG. 14a represent a range of targeting options that relate to an exemplary distally located locking range in an exemplary IMN. This range of locking options can be secured by the self-tightening, spring-loaded, clamping mechanism, such as a modified Corbin clamp. The clamp could have a slot that mates with pins 955 and the Corbin clamp can be used to secure a position within the desired range such as seen in the exemplary middle slots 975 in FIG. 14a.

Figure 16B:
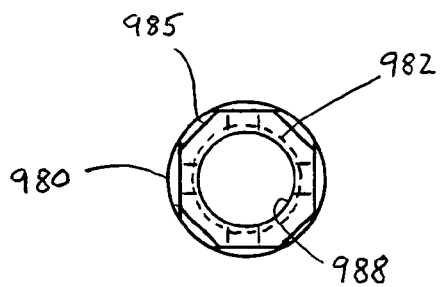
FIGS. 16a-b show plan and top views, respectively, of a locking collar in accordance with an embodiment of the current invention.
Figure 16A:
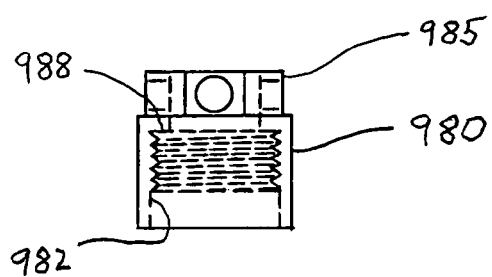

As seen more particularly in FIGS. 16a-b, locking collar 980 is provided with an inner threaded portion 982 and a locking collar flange 988. Thus, when the target probe assembly 900 is mounted onto the nail adaptor 200 it preferably threaded onto the male threaded end 120 of the nail adaptor 100. Additionally, the locking collar 980 is preferably provided with a tool mounting surface 985 as shown in FIGS. 16a and b. Alternatively, the tool mounting surface could be on the outer cylindrical portion of the locking collar 980. Further, the locking collar 980 is preferably provided with a locking collar flange 988, which should hold the first and second alignment tabs 962, 964 onto the proximal end of the nail adaptor 920. As seen more particularly in FIG. 14c, the alignment tabs 962 are preferably made of different widths that correspond to the width of the first and second alignment slots 112, 114 of the nail adapter 100. When mounted, the alignment tabs 962, 964 preferably mate with the corresponding alignment slots 112, 114. This ensures that the target sensor probe assembly 900 is mounted onto the nail adapter 100 in a reliable predefined configuration.

In the preferred embodiment, the locking collar 980 is integrally fixed to the distal portion of the probe cylinder 960. Alternatively, the locking collar 980 can be a separate element. However, if separate, a locking collar 980 as seen in FIG. 15a would need to be mounted onto the probe cylinder 960 prior to inserting the probe rod sub assembly shown in FIG. 13a into the probe cylinder 960. This is also preferably done prior to the installation of mounting cap 968. However, both the mounting cap 968 and the probe rod handle 925 could be designed with a narrower profile in order to allow a separate locking collar 980 to be installed as the last part of the target sensor probe assembly 900.

FIGS. 20 and 21 show a sensor calibration probe 990, which has a similar design to that of the target sensor probe assembly 900. The primary distinction is that rather than delivering a target sensor 905, the sensor calibration probe 990 measures the surgically implanted position of the target receiving bores 13, 15. This calibration helps to estimate the degree of deflection and deformation that has occurred in the IMN 10 as a result of the implantation in the medullary canal. The distal portion of the probe assembly 990 includes a target locking tab 993, which is used to measure the position of the distal target holes. The target locking tab 993 is radially biased, preferably by a distal positioning guide 997, such that it presses against the inner walls of the IMN 10 while passing through it. In this way, when target locking tab 993 is axially and rotationally aligned with a target receiving bore 13, 15 it will snap into the hole. Once a position is found, the calibration markings 997 are used to measure or estimate the deflection that has occurred at the distal end of the IMN 10. This information can then be used, if needed, to recalibrate the target sensor probe assembly 900 which in turn is used to establish the final position of the targeting console 800. Also, the tapered profile of the target locking tab 993 allows for extraction from any target receiving bore 13, 15 by advancing the probe beyond the hole and rotating it out of alignment with the hole. Once the locking tab 993 is not aligned with an IMN 10 hole it can be easily withdrawn. Even though rotational deflection is the least occurring deflection, additional lateral slots could be added to guide 997. In this way rotational deformation can reliably be determined and calibrated on a sensor probe designed with some of the same allowances as the sensor calibration probe 905.

FIG. 22 shows a combination position pin and Allen wrench tool 405. This tool 405 can also be used to loosen and tighten lighter weight lower profile fixing screws. Further, the profile of the bends on the combination position pin and Allen wrench tool 405 can be tighter creating a lower profile tool for use in tighter places.

Figure 23:
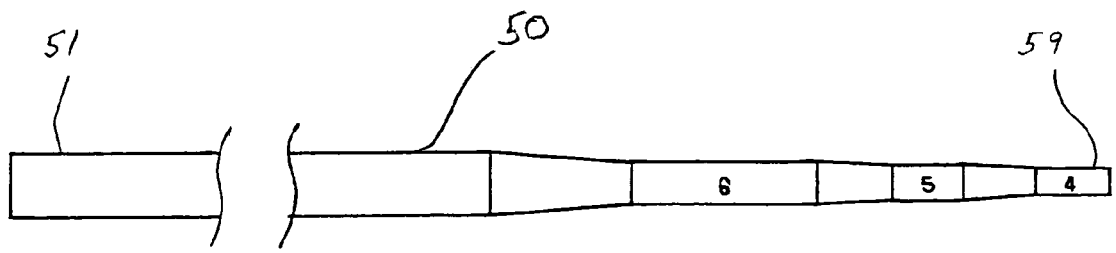
FIG. 23 shows a drift-pin in accordance with an embodiment of the current invention.

FIG. 23 shows a drift pin 50 in accordance with an embodiment of the current invention. The drift-pin which is also referred to as an alignment pin, is used to preliminarily adjust and align the targeting and securing assembly shown in FIG. 1. The drift pin 50 allows a selected IMN 10 to be pre-targeted before it is implanted into the patient. The first end 51 of the drift pin 50 is preferably inserted into one of the mounting holes 736 on the distal targeting head 700. While the first end 51 is still in one of the mounting holes 736 in the distal targeting head 700, the second end 59 of the drift-pin 50 is then inserted into a select target hole in the IMN 10. The drift-pin lines up the chosen mounting hole 736 in the distal targeting head 700 with the target receiving bore 13, 15 or a locking position in a given IMN 10. Once the drift pin aligns these elements, the fixing screws on the overall assembly can be tightened, securing the assembly. Thereafter, the positions of the targeting head 700, head coupling 600, targeting arm 500 and bridge adapter 400 relative to their position on the nail adapter 100 is tracked/preserved, preferably by using the tracking collar 380 (seen in FIGS. 24a-c) with the nail adapter 100. Mounting such a collar 380 marks an estimated targeting position for the later return of the pre-targeted assembly, including the bridge adapter 400, distal targeting arm 500, head coupling 600, and distal targeting head 700. All elements of the targeting arm assembly can remain modularly assembled and set aside for re-assembly after nail implantation takes place at which time the pre-constructed modular aspects of the targeting arm assembly are repositioned to the position preferably preserved by the location fixing element 380. Once the fixing element 380 is secured, the drift pin 50 is preferably removed and the IMN 10 is implanted in the patient. It is to be understood that many most intramedullary nails can deflect upon implantation so the exact pre-targeted position identified above may no longer be accurate. However, the general proximity and approximate configuration of the assembly will preferably have been pre-determined, thus facilitating more rapid target location time. It is also understood that this procedure is typically only used on distal locking positions of adequate length to cause deflection. The drift-pin is preferably step-tapered to compensate for varying intramedullary nail aperture diameters but can be made to target a single nail aperture dimension.

Figure 24B:
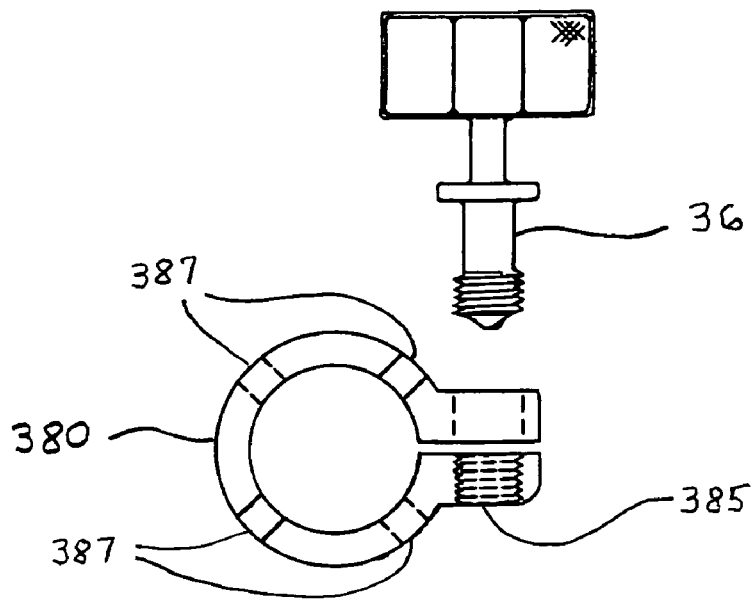
FIGS. 24a-c show plan, left side and top views, respectively, of a tracking collar in accordance with an embodiment of the current invention.
Figure 24C:
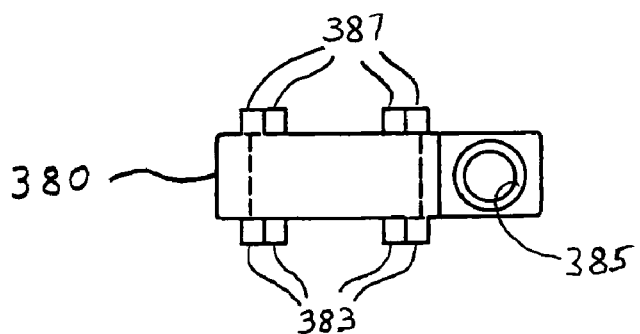
Figure 24A:
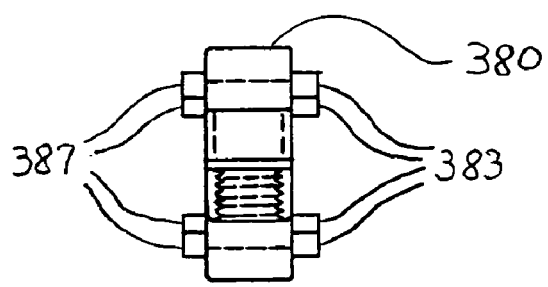
Figure 25A:
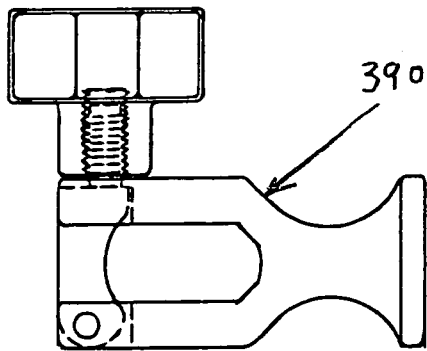
FIGS. 25a-e show various views of an additional location fixing element in accordance with an embodiment of the current invention.
Figure 25B:
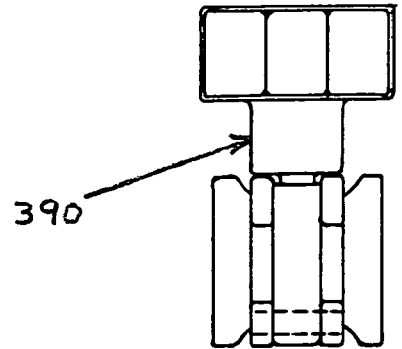
Figure 25C:
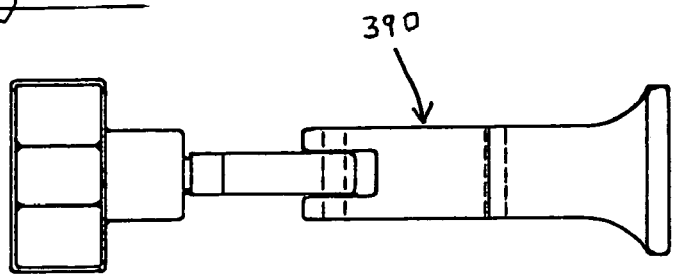
Figure 25D:
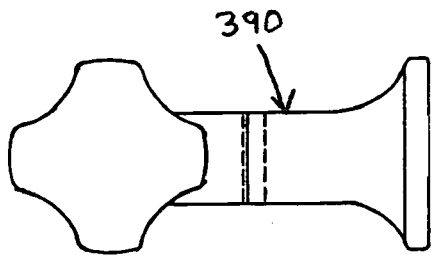
Figure 25E:
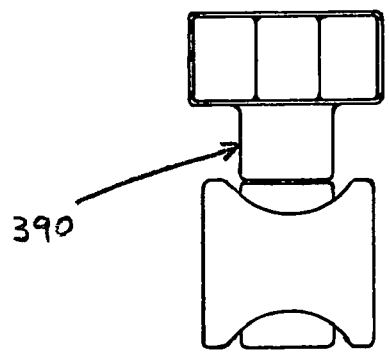

During the preliminary phase of estimating the configuration of the targeting arm assembly may be is beneficial to employ position tracking tools that will indicate or mark the estimated position of the modular parts. FIGS. 24a-c show an example of one such position tracking tool, namely a tracking collar 380. Such a tracking collar 380 preferably includes interlocking tabs 383, 387 that mate with either of the interlocking recesses 433, 437 on the mounting collar 440. Each of two sides 431, 439 of the mounting collar, preferably has one set of interlocking recesses. Once one set of the tabs 383, 387 are mated with one set of the recesses 433, 437, a fixing screw 36 can be applied in the female threaded bore 385 to clamp the tracking collar 380 onto the mounting portion 140 of the nail adapter 100. Alternatively, the tracking collar 380 could have a hinged design (not shown) to allow easier re-positioning/positioning on the nail adapter 100. In either embodiment, the tracking collar 380 can be applied proximally or distally relative to the cylindrical mounting collar 440 on the bridge adapter 400.

A proximity shim 390 (not shown) can be mounted between the tracking collar 380 and the cylindrical mounting collar 400 of the targeting arm adapter 400 to facilitate a more rapid distal locking sequence in the event that more than one distal locking position needs to be targeted. Proximity shims can take the form of a collar that is adapted to be mounted on the cylindrical mounting portion 140. Alternatively, the proximity shims can have a semi-circular or split-ring design that can easily be snapped onto the nail adapter 100. The shims are generally exploited in such a way as to reposition the assembly to target a more proximal distal locking hole/slot position (in the case of sensor delivery probe application). In fact, the shims can alternatively come in other shapes, as long as they can still serve this function. Pre-positioned sensors implanted in an IMN allow the shims to be exploited in such a way as to advance the assembly toward a more distal locking hole position, if desired. Another benefit of being able to remove and precisely reposition various portions of the assembly is that an effected area of a patient's limb could possibly be more easily accessible to a clinician allowing access to incision points pinpointed by the present system.

The locking position proximity shims are shims that are exploited after the first distal locking hole has successfully been targeted. Once an initial position has been targeted, the known distance and line to the next proximally located distal hole is generally known. For example, an IMN can have a 10 mm in-line distance between the center of one distal hole to the next distal hole. In such a case, a 10 mm shim with tabs (not shown) such as those interlocking tabs 383, 387 found on the fastening collar 380 can be provided that preferably mate with either of the interlocking recesses 433, 437 on the mounting collar 440. The tracking collar 380 can be positioned on the other side of the shim that can have interlocking recesses 433, 437 such as those found on the mounting collar. In this way, a fixed mounting collar 400, a shim and a tracking collar 380 are all mounted on the nail adapter 100. Loosening the mounting collar and removing the shim allows the mounting collar to slide (with recesses (precisely 10 mm in-line from the previously targeted distal locking hole) to the engage the interlocking tabs 383, 387 of the tracking collar 380.

FIGS. 25*a*-*e* show a second tracking collar 390 designed to engage with the mounting shaft 460 of the bridge adapter 400 that is used to facilitate rapid and precise repositioning of a given distal targeting arm after it was removed following the pre-surgical assembly positioning estimate. Alternatively, it may be beneficial for the second tracking collar 390 engaged with the mounting shaft 460 of the bridge adapter 400 to be used in conjunction with a given proximal targeting arm thus facilitating rapid and precise repositioning of a given proximal targeting arm further facilitating proximal locking.

The present invention also provides accessories for the preliminary step of properly seating the IMN 10 in a medullary canal of a bone. In this regard, FIGS. 26*a*-*c* show a tamping collar assembly 300, which is preferably used for the final positioning of the IMN 10. In one application, the tamping collar 300 is placed on the proximal end of the nail adaptor 100. Thus, prior to assembling the bridge adapter 400 onto the nail adaptor 100, as discussed above, the tamping collar assembly 300 is preferably used. Once the tamping collar 300 is mounted, a lock nut 125 is preferably screwed onto the proximal nail threading 120 of the nail adaptor 100. The tamping collar 300 is provided with a tubular portion 310 which is preferably designed to fit snugly on the outer surface of the cylindrical mounting portion 140 of the nail adaptor 100. The tamping collar 300 is also provided with a radially inward projecting flange 315, which preferably engages with the stepped configuration at the proximal end of the nail adaptor 100 between the male threaded portion 120 and the cylindrical mounting portion 140. Additionally, the tamping collar 300 is provided with a tamping rod mount 320, which includes a tamping rod seat 322. The tamping rod mount 320 includes the female threaded recess preferably designed to receive a male threaded end 352 of a tamping rod 350.

FIGS. 28*a*-*c* show more details of the tamping rod 350. The tamping rod 350 is preferably cannular to provide access to the inner cannular portion of the coupler rod 200 and the attached IMN 10, to allow for alternative methods of nail insertion. Once mounted, a hammer or other blunt tamping member is preferably used on the strike plate 358. Thus, the pressure of the impact from such a hammer strike is evenly distributed onto the IMN 10. This allows the IMN 10 to be properly positioned, while minimizing any damage to it or the patient. It is preferable that both the tamping collar 300 and the tamping rod 350 be provided with tool mounting surfaces 325, 355. Also the tamping collar 300 can be provided with a fixing screw hole 330 in which a fixing screw 31 can be applied to not only further secure the tamping collar onto the end of the nail adaptor 100, but also to properly align it on the nail adaptor using fixing screw grooves 135 previously described on the nail adaptor.

The present system also provides various means for achieving nail insertion. The tamping collar 300 provides offset tamping surfaces during nail insertion, while providing full access to the cannular features of the IMN, the nail adapter 100, and the coupler rod 200. Further, nail insertion can be achieved by hand driven insertion where applicable by attaching the bridge adapter 400 securely to the cylindrical mounting portion 140 of the nail adapter 100 by means of a fixing screw 32. The bridge adapter 400 is then used as a hand-hold to provide leverage or pressure to the IMN 10 for insertion, removal or repositioning. Additionally, tamping rod 350 may be attached to the female threading 220 of the coupler rod 200 allowing for axial, rather than offset tamping. Nail extraction and/or repositioning can in its most primitive form can be achieved, by pulling on the tamping rod 350 in this configuration. Alternatively, a slide hammer used in conjunction with an extraction extension or other similar surgical instrument could be used for removal/repositioning if necessary. Postoperative nail extraction will follow standard operating procedures or could be added to this platform.

FIGS. 27*a*-*b* show more detail of the locking nut 125. Particularly, the locking nut 125 preferably includes a tool recess 127 and inner threading 129 designed to mate with the threaded end of the nail adaptor 120. Alternatively, a more traditional locking nut that uses a standard wrench for tightening and loosening could be employed.

Figure 29C:
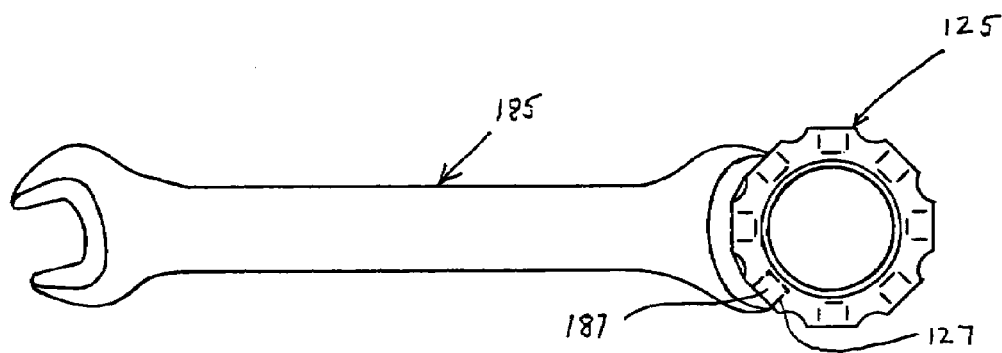
FIGS. 29a-c show plan and top views of modified wrench, as well as the wrench engaged on a locking nut in accordance with an embodiment of the current invention.
Figure 29B:
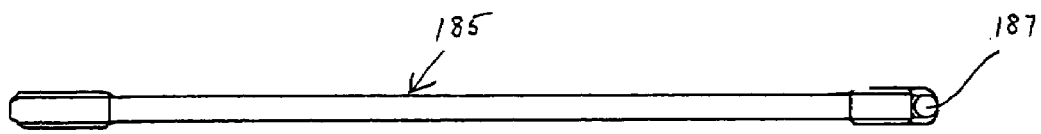
Figure 29A:
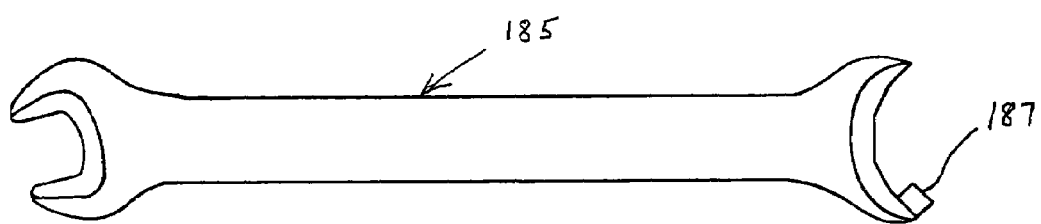

FIGS. 29*a*-*c* show the preferred embodiment of a modified wrench 185 that can be used on the tool mounting surfaces 215, 325, 355, 985. This modified wrench 185 includes a protruding key element 187 adapted to mate with the tool recess 127 described above, particularly with respect to the locking nut 125. It is understood in the art that other wrenches of traditional design may be exploited by the present system.

It should be noted that the overall length of each element of the assembly, tools and accessories discussed above can be manufactured to alter the dimensions shown, making them smaller or larger. Also, the materials, coatings or finishes on any materials used, while preferably lightweight and durable, could be changed or altered to suit the environment or application of the present invention. Many of the elements of the present system are predominantly a surgical grade stainless steel (those generally used in the manufacture of surgical instruments). Thus, the nail adapter 100, tamping elements 300, position tracking elements 380, 390, bridge adapter 400, coupler rod 200, bolts, wrenches, head coupling 600, position pin 50, drift pin 405, tamping rod 350, fixing screws, and the mounting collars/extensions attached to distal/proximal ends of targeting arms 500, 502, 503 are preferably made from such stainless steel. However, the distal and proximal targeting arm body 530, 534, 536 and targeting head 700 are preferably constructed from a durable lightweight artifact free radial lucent material, such as carbon fiber laminate. Also, the electronic targeting console is preferably an electronic handheld device. Some aspects, such as the extension rod 910, proximity shims 390 and extension probe rod guide washers 930, 950 in the sensor delivery probe 900 can be constructed from a suitable plastic such as high density polyethylene (HDPE). Additionally, various components, for example, the bridge adapter 400 can potentially have material removing or machining done to them in an effort to reduce the weight of a given component of the present system while retaining the structural integrity of a given component.

While the invention has been described in connection with one or more embodiments, it is to be understood that the specific mechanisms and techniques which have been described or shown are for illustrative purposes only to provide a basic understanding of the invention, and that many modifications may be made to the invention described without deviating from the scope of the invention. Thus, the scope of the invention should be determined by the appended claims and their legal equivalents, rather than by the examples given.

What is claimed is:

1. A device adapted to determine a targeting position on a surgically implantable nail adapted to be used in internal fixation of a bone, the nail comprising a distal end and a proximal end, the device comprising:
   an extension rod comprising a longitudinal axis and adapted to be detachably coupled to the proximal end of the nail;
   a bridge member adjustably secured to the extension rod and extending a length radially from the longitudinal axis of the extension rod, a position of the bridge member on the extension rod being rotationally and longitudinally adjustable with respect to the longitudinal axis of the extension rod;

a targeting arm adjustably mounted on the bridge member and extending from the bridge member toward the distal end of the nail, wherein more than one location is provided along the length of the bridge member for said mounting of the targeting arm on the bridge member, the targeting arm comprising a drill guide, wherein the targeting arm is slidably mounted along the length of the bridge member to vary the distance between the targeting arm and the extension rod; and a targeting probe adapted to be inserted through the extension rod substantially to a distal portion of the nail.

2. A device as defined by claim 1, wherein the bridge member is directly secured to the extension rod for selecting the position of the bridge member on the extension rod.

3. A device as defined by claim 1, wherein a position of the drill guide on the targeting arm is rotatably adjustable relative to the targeting arm, the drill guide being positioned closer to the distal end of the nail than to the proximal end of the nail.

4. A device as defined by claim 1, wherein the drill guide is pivotally supported by the targeting arm.

5. A device as defined by claim 1, wherein the bridge member is reversibly mounted on the extension rod in a position along the longitudinal axis of the extension rod, the reversible mounting including at least one of a first orientation and a second orientation, a distal end of the targeting arm being closer to the distal end of the nail in the first orientation than in the second orientation.

6. A device as defined by claim 1, wherein the targeting arm positions a targeting system, the targeting system indicating alignment between the drill guide and the targeting position on the nail.

7. A device as defined by claim 1, wherein the targeting arm includes at least one through-hole whereby at least a portion of the bridge member disposed within the targeting arm collar is visible through the through-hole.

8. A device adapted to determine a targeting position on a surgically implantable nail adapted to be used in internal fixation of a bone, the nail comprising a distal end and a proximal end, the device comprising:

an extension rod comprising a longitudinal axis and adapted to be detachably coupled to the proximal end of the nail;

a bridge member adjustably secured to the extension rod and extending a length radially from the longitudinal axis of the extension rod, a position of the bridge member on the extension rod being rotationally and longitudinally adjustable with respect to the longitudinal axis of the extension rod; and a targeting arm adjustably mounted on the bridge member and extending from the bridge member toward the distal end of the nail, wherein more than one location is provided along the length of the bridge member for said mounting of the targeting arm on the bridge member, the targeting arm comprising a drill guide, wherein the targeting arm is slidably mounted along the length of the bridge member to vary the distance between the targeting arm and the extension rod, wherein the bridge member includes a bridge member collar for receiving the extension rod, wherein at least a portion of the extension rod is mounted inside the bridge member collar.

9. A device as defined by claim 8, wherein the bridge member collar includes at least one through-hole whereby at least a portion of the extension rod disposed within the bridge member collar is visible through the through-hole.

10. A device as defined by claim 8, wherein the bridge member is directly secured to the extension rod for selecting the position of the bridge member on the extension rod.

11. A device as defined by claim 8, wherein a position of the drill guide on the targeting arm is rotatably adjustable relative to the targeting arm, the drill guide being positioned closer to the distal end of the nail than to the proximal end of the nail.

12. A device as defined by claim 8, wherein the drill guide is pivotally supported by the targeting arm.

13. A device as defined by claim 8, wherein the bridge member is reversibly mounted on the extension rod in a position along the longitudinal axis of the extension rod, the reversible mounting including at least one of a first orientation and a second orientation, a distal end of the targeting arm being closer to the distal end of the nail in the first orientation than in the second orientation.

14. A device as defined by claim 8, wherein the targeting arm positions a targeting system, the targeting system indicating alignment between the drill guide and the targeting position on the nail.

15. A device as defined by claim 8, further comprising a targeting probe adapted to be inserted through the extension rod substantially to a distal portion of the nail.

16. A device adapted to determine a targeting position on a surgically implantable nail adapted to be used in internal fixation of a bone, the nail comprising a distal end and a proximal end, the device comprising:

an extension rod comprising a longitudinal axis and adapted to be detachably coupled to the proximal end of the nail;

a bridge member adjustably secured to the extension rod and extending a length radially from the longitudinal axis of the extension rod, a position of the bridge member on the extension rod being rotationally and longitudinally adjustable with respect to the longitudinal axis of the extension rod; and a targeting arm adjustably mounted on the bridge member and extending from the bridge member toward the distal end of the nail, wherein more than one location is provided along the length of the bridge member for said mounting of the targeting arm on the bridge member, the targeting arm comprising a drill guide, wherein the targeting arm is slidably mounted along the length of the bridge member to vary the distance between the targeting arm and the extension rod, wherein the bridge member includes a curved section extending between the extension rod and the targeting arm, the curved section extending radially outwardly from the longitudinal axis of the extension rod, the curved section also curving towards a direction parallel to the longitudinal axis of the extension rod.

17. A device as defined by claim 16, wherein the bridge member is directly secured to the extension rod for selecting the position of the bridge member on the extension rod.

18. A device as defined by claim 16, wherein a position of the drill guide on the targeting arm is rotatably adjustable relative to the targeting arm, the drill guide being positioned closer to the distal end of the nail than to the proximal end of the nail.

19. A device as defined by claim 16, wherein the drill guide is pivotally supported by the targeting arm.

20. A device as defined by claim 16, wherein the bridge member is reversibly mounted on the extension rod in a position along the longitudinal axis of the extension rod, the reversible mounting including at least one of a first orientation and a second orientation, a distal end of the targeting arm being closer to the distal end of the nail in the first orientation than in the second orientation.

21. A device as defined by claim 16, wherein the targeting arm positions a targeting system, the targeting system indicating alignment between the drill guide and the targeting position on the nail.

22. A device as defined by claim 16, further comprising a targeting probe adapted to be inserted through the extension rod substantially to a distal portion of the nail.

23. A device adapted to determine a targeting position on a surgically implantable nail adapted to be used in internal fixation of a bone, the nail comprising a distal end and a proximal end, the device comprising:
- an extension rod comprising a longitudinal axis and adapted to be detachably coupled to the proximal end of the nail;
- a bridge member adjustably secured to the extension rod and extending a length radially from the longitudinal axis of the extension rod, a position of the bridge member on the extension rod being rotationally and longitudinally adjustable with respect to the longitudinal axis of the extension rod; and
- a targeting arm adjustably mounted on the bridge member and extending from the bridge member toward the distal end of the nail, wherein more than one location is provided along the length of the bridge member for said mounting of the targeting arm on the bridge member, the targeting arm comprising a drill guide, wherein the targeting arm is slidably mounted along the length of the bridge member to vary the distance between the targeting arm and the extension rod, wherein the targeting arm includes a targeting arm collar for receiving a portion of the bridge member, wherein at least a portion of the bridge member is mounted within the targeting arm collar.

24. A device as defined by claim 23, wherein the bridge member is directly secured to the extension rod for selecting the position of the bridge member on the extension rod.

25. A device as defined by claim 23, wherein a position of the drill guide on the targeting arm is rotatably adjustable relative to the targeting arm, the drill guide being positioned closer to the distal end of the nail than to the proximal end of the nail.

26. A device as defined by claim 23, wherein the drill guide is pivotally supported by the targeting arm.

27. A device as defined by claim 23, wherein the bridge member is reversibly mounted on the extension rod in a position along the longitudinal axis of the extension rod, the reversible mounting including at least one of a first orientation and a second orientation, a distal end of the targeting arm being closer to the distal end of the nail in the first orientation than in the second orientation.

28. A device as defined by claim 23, wherein the targeting arm positions a targeting system, the targeting system indicating alignment between the drill guide and the targeting position on the nail.

29. A device as defined by claim 23, further comprising a targeting probe adapted to be inserted through the extension rod substantially to a distal portion of the nail.

* * * * *